(12) United States Patent
Tzeng

(10) Patent No.: US 7,412,993 B2
(45) Date of Patent: Aug. 19, 2008

(54) EXPANDABLE STENT

(76) Inventor: George Tzong-Chyi Tzeng, 27 Briarbrook Dr., Briarcliff Manor, NY (US) 10510

( * ) Notice: Subject to any disclaimer, the term of this patent is extended or adjusted under 35 U.S.C. 154(b) by 494 days.

(21) Appl. No.: 10/796,795

(22) Filed: Mar. 9, 2004

(65) Prior Publication Data

US 2005/0203610 A1  Sep. 15, 2005

(51) Int. Cl.
*A61F 2/06* (2006.01)
(52) U.S. Cl. ............... 140/149; 72/135; 72/371; 72/372; 623/1.15; 623/1.16; 623/1.22; 606/194; 140/92.1; 140/71 R
(58) Field of Classification Search ............ 72/66, 72/135, 137, 138, 371, 372; 623/1.1, 1.35, 623/1.5, 1.53, 1.16, 1.15, 1.22; 606/194, 606/195, 191, 198; 140/92.1, 71 R, 149
See application file for complete search history.

(56) References Cited

U.S. PATENT DOCUMENTS

| | | | | |
|---|---|---|---|---|
| 5,334,217 A * | 8/1994 | Das | | 606/213 |
| 5,607,445 A * | 3/1997 | Summers | | 623/1.22 |
| 5,639,277 A * | 6/1997 | Mariant et al. | | 606/191 |
| 5,643,339 A * | 7/1997 | Kavteladze et al. | | 623/1.22 |
| 5,843,176 A * | 12/1998 | Weier | | 623/1.2 |
| 6,409,750 B1 | 6/2002 | Hyodoh et al. | | |
| 6,497,724 B1 * | 12/2002 | Stevens et al. | | 623/1.15 |
| 6,699,279 B2 * | 3/2004 | Stevens et al. | | 623/1.15 |
| 6,821,291 B2 * | 11/2004 | Bolea et al. | | 623/1.11 |
| 7,048,014 B2 * | 5/2006 | Hyodoh et al. | | 140/92.1 |
| 7,128,755 B2 * | 10/2006 | Su et al. | | 623/1.15 |
| 2002/0183830 A1 | 12/2002 | Su et al. | | |
| 2005/0229998 A1 * | 10/2005 | Pollock-Kueny | | 140/118 |

OTHER PUBLICATIONS

Shih-Horng Su. "New Expandable Biodegradable Polymeric Endovascular Stent Designs". The University of Texas at Arlington, Doctor of Philosophy Thesis, Chapter 2, pp. 38-49, Aug. 2000.

* cited by examiner

*Primary Examiner*—Dmitry Suhol
(74) *Attorney, Agent, or Firm*—Occhiuti Rohlicek & Tsao LLP

(57) ABSTRACT

A medical apparatus is fabricated by providing a coil that has a plurality of primary loops along a longitudinal direction, and for each of one or more of the primary loops, forming one or more secondary loops on the primary loop.

6 Claims, 20 Drawing Sheets

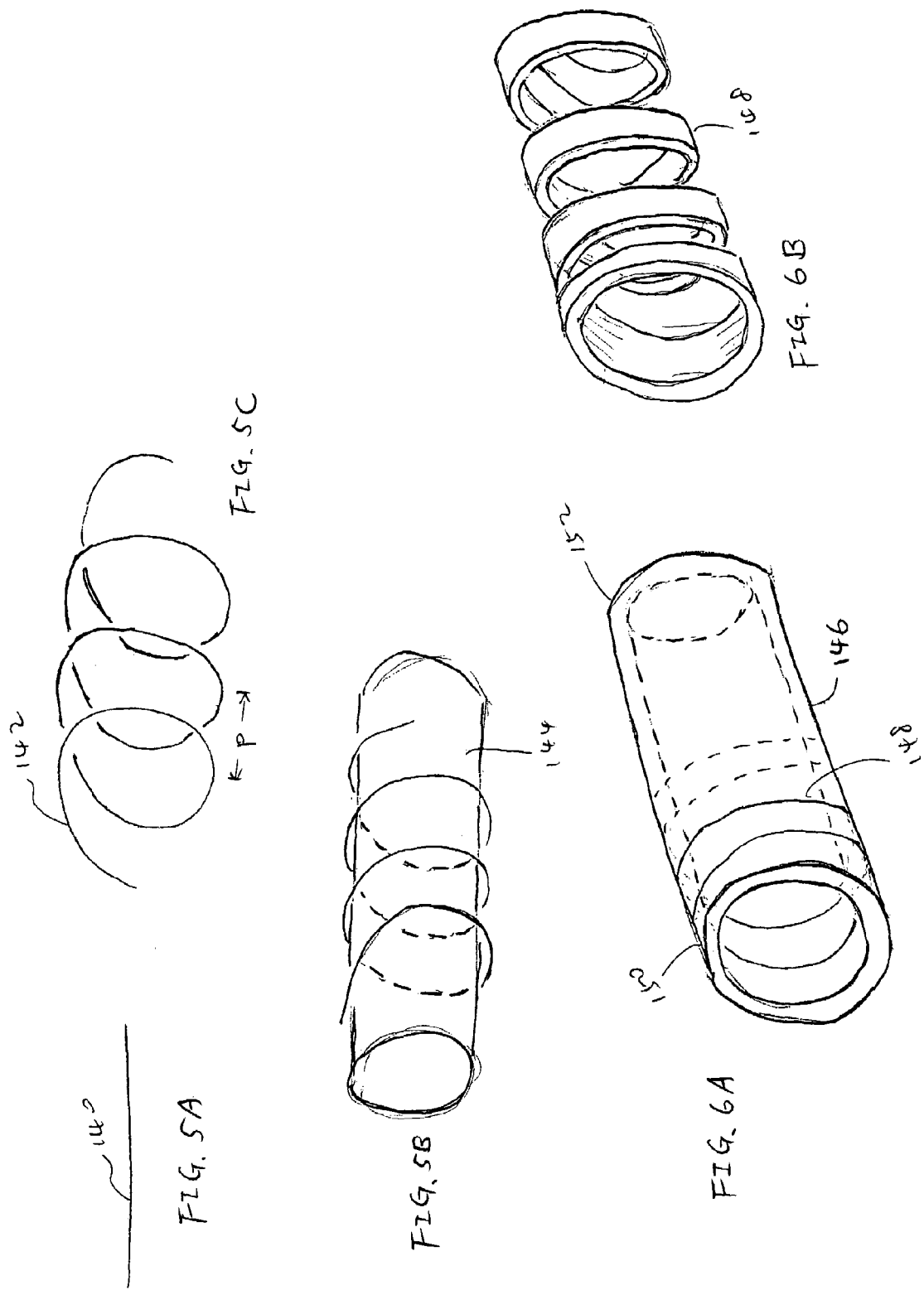

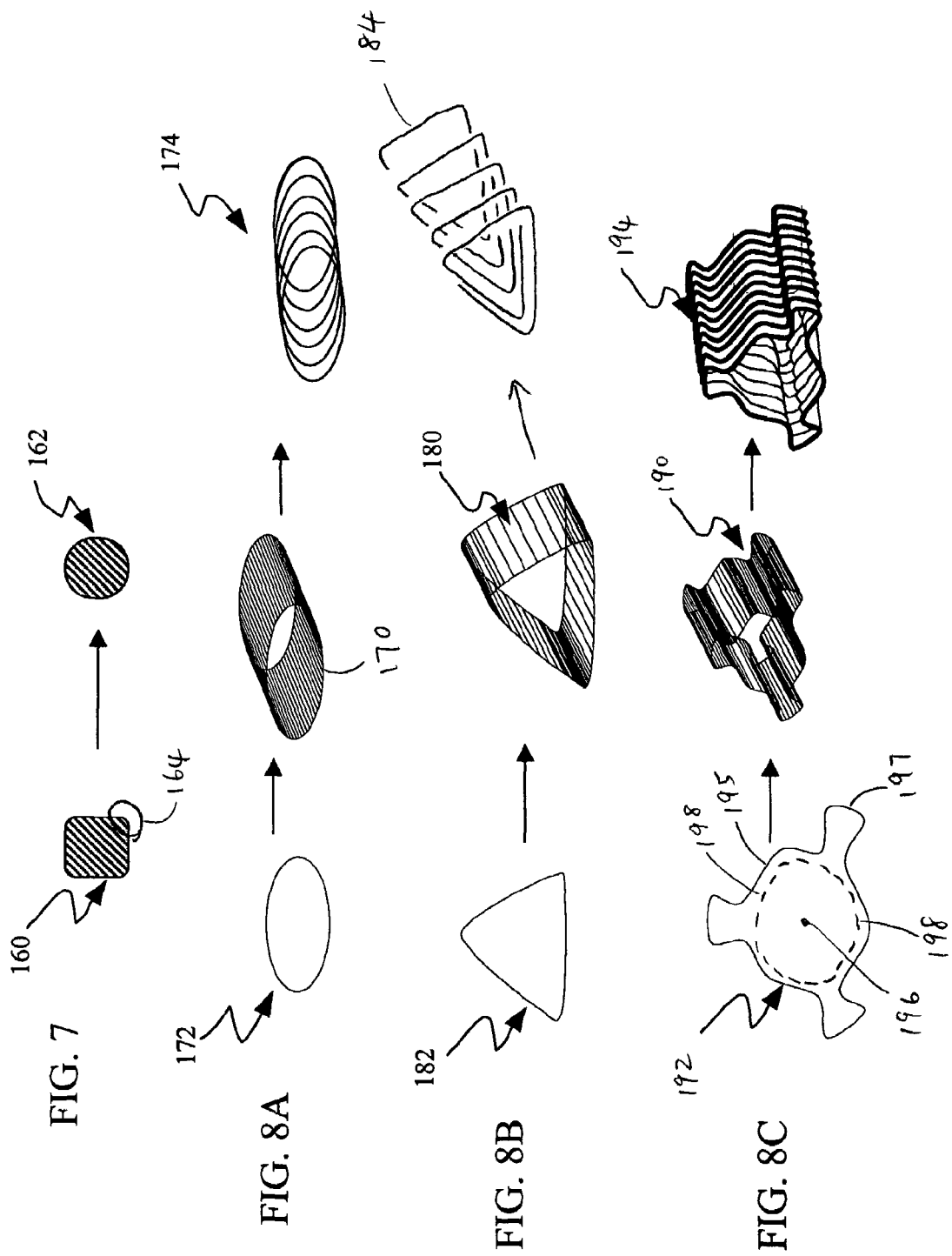

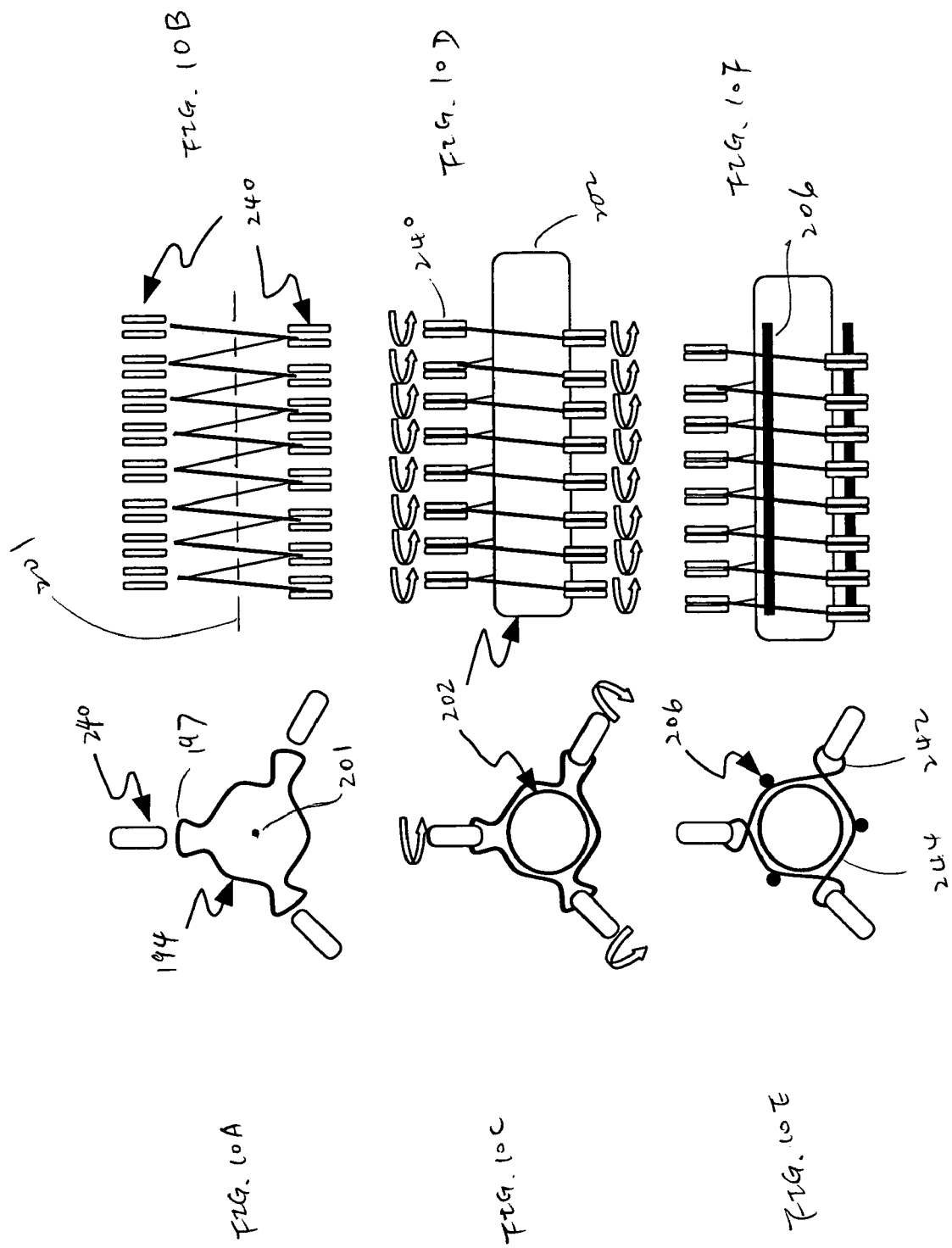

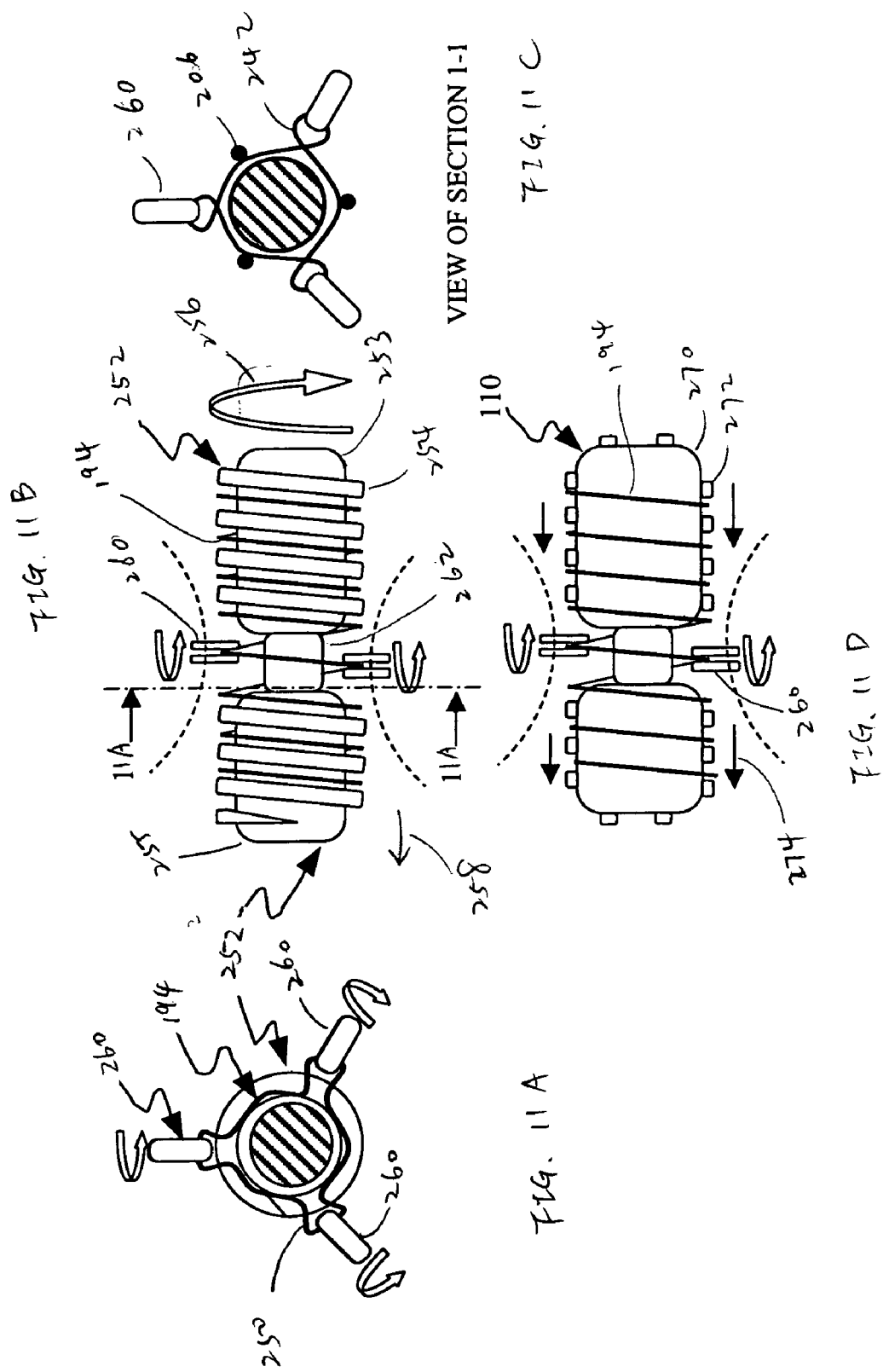

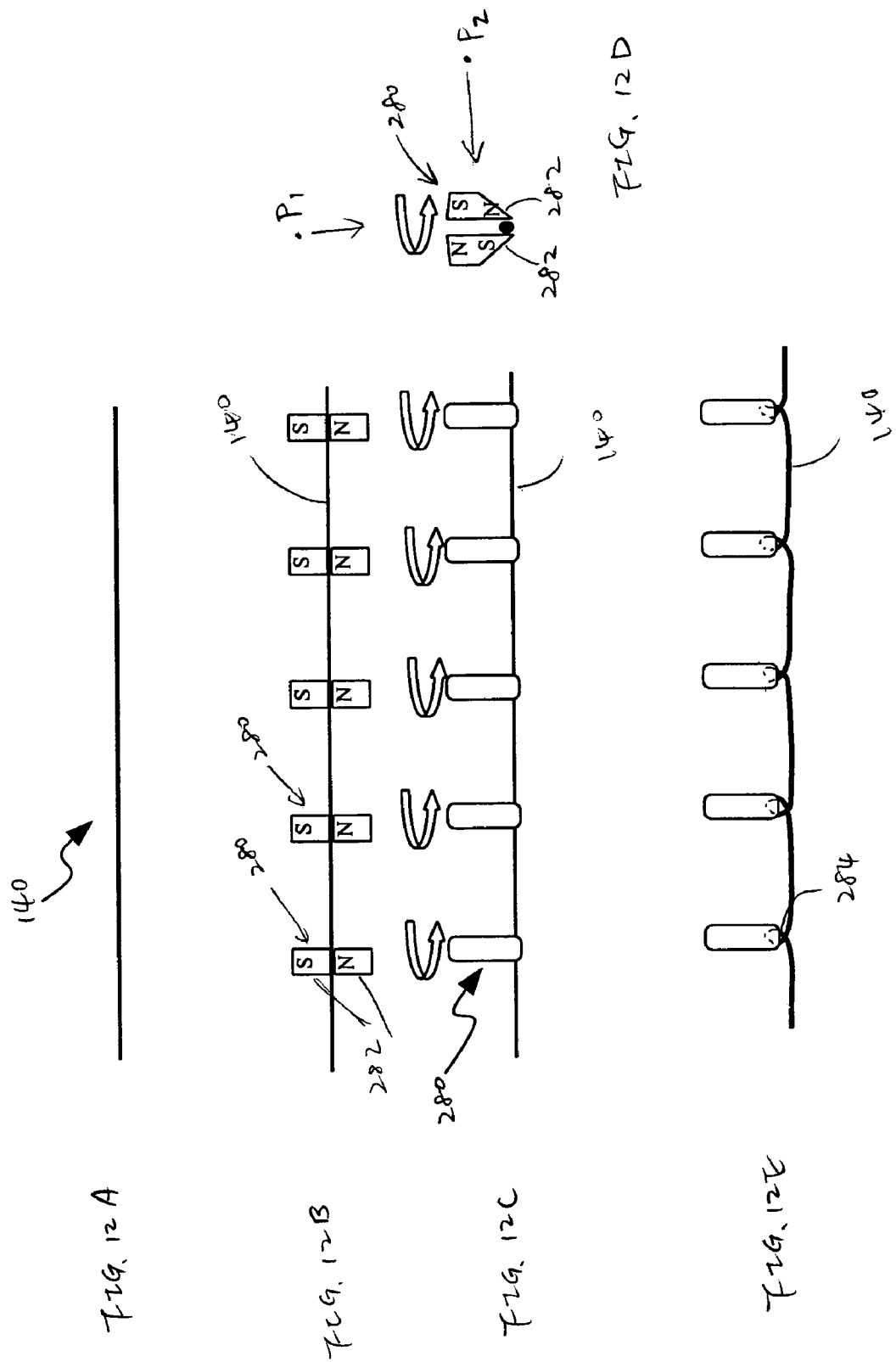

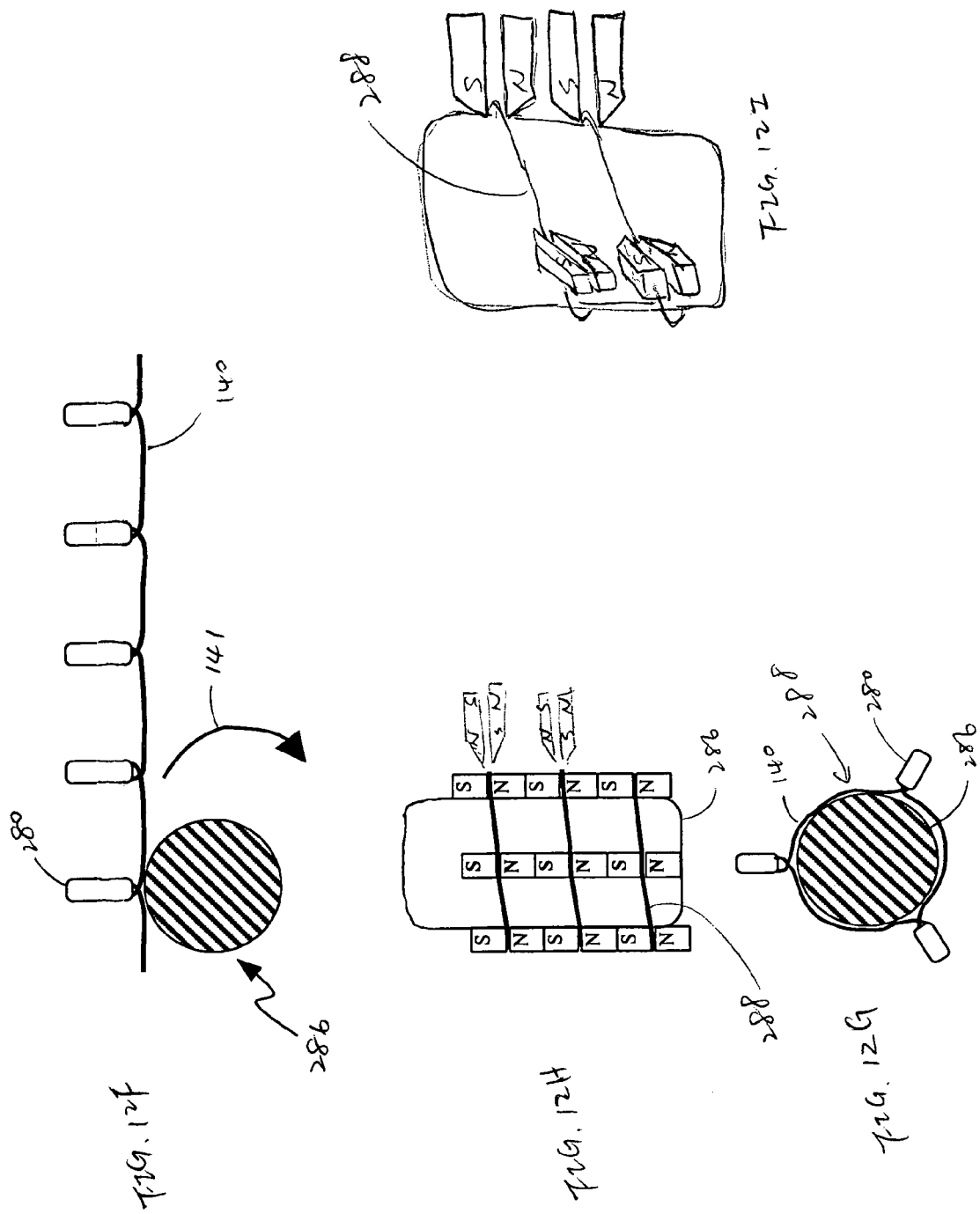

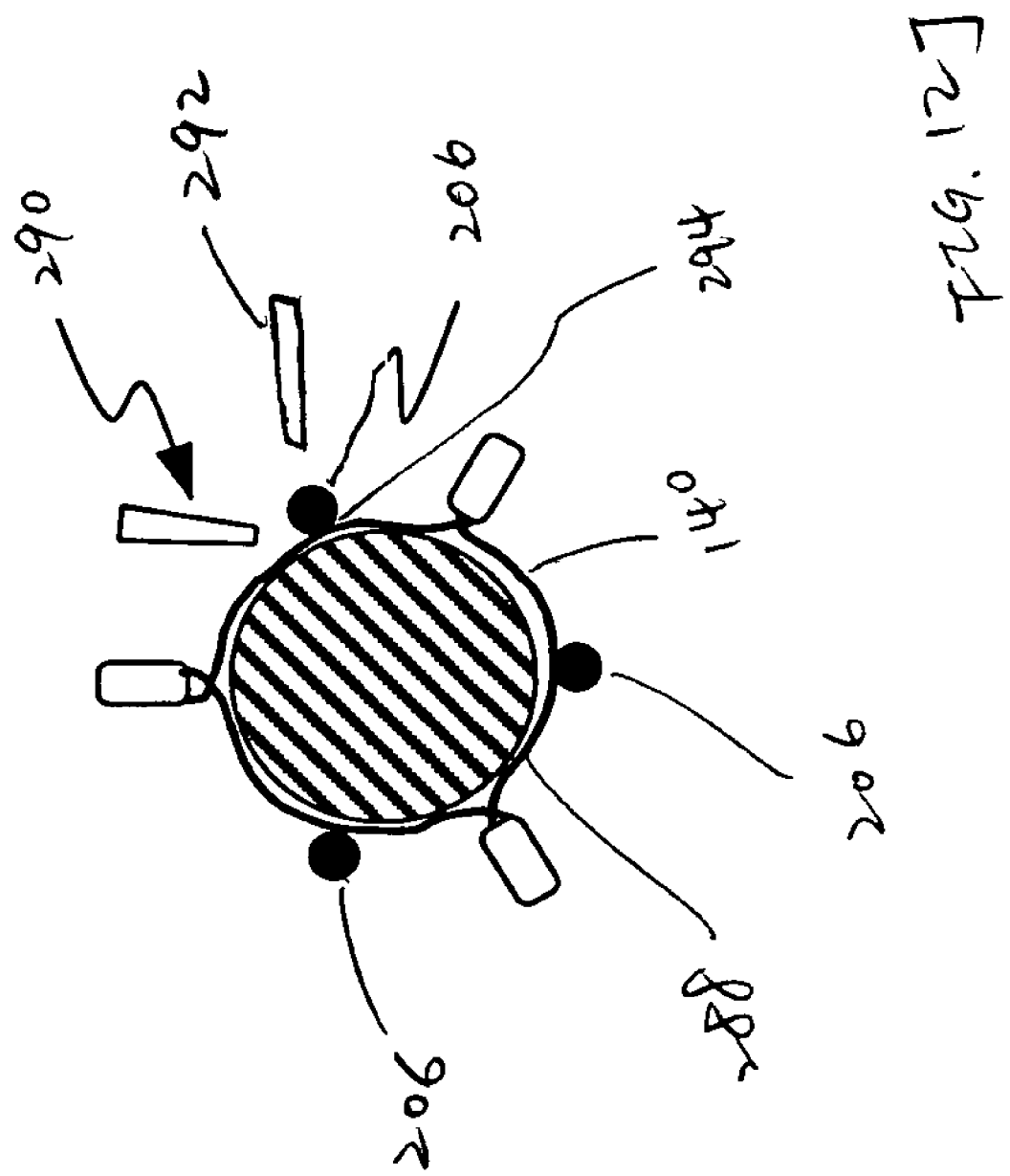

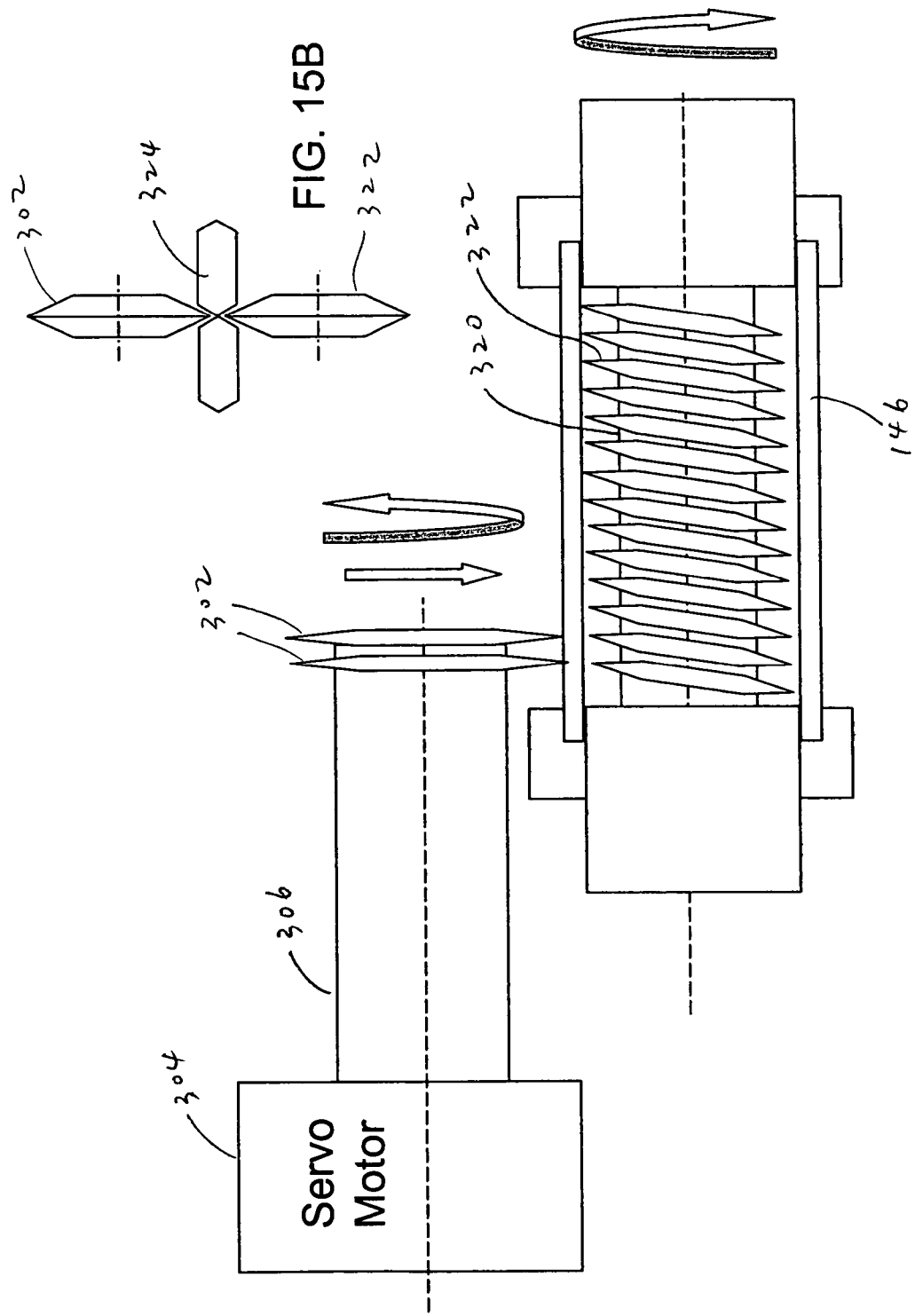

EXPANDABLE STENT

BACKGROUND

This invention relates to expandable stents.

A multi-loop expandable stent can be implanted in arteries or body passageways to treat strictures or to prevent occlusion. The stent can also be used to deliver therapeutic agents to lesion sites. The stent is initially collapsed and has a smaller cross section to allow easy insertion into the artery or body passageways. An inflatable balloon or an expandable device is placed within the stent, and after the stent is positioned at the proper location in the artery or passageways, the balloon or the expandable device expands the stent. When the balloon or expandable device is retracted, a passageway is formed by the expanded stent.

SUMMARY

In general, in one aspect, the invention features a method that includes generating a medical apparatus by providing a coil including a plurality of primary loops along a longitudinal direction, and for each of one or more of the primary loops, forming a secondary loop on the primary loop.

Implementations of the invention may include one or more of the following features.

The coil includes a helical coil.

Forming the secondary loop on the primary loop includes twisting a portion of the primary loop to form the secondary loop.

Twisting a portion of the primary loop includes gripping a portion of the primary loop using a clip and rotating the clip to twist the portion of the primary loop.

The clip includes magnetized portions having different polarities.

The magnetized portions are disposed at the tips of the clip that contact the primary loop or the secondary loop.

The clip includes tips that contact the primary loop and handles that allow manipulation of the clip, the magnetized portions being disposed at the handles.

The method includes, for each of one or more primary loops, using a clip to grip a portion of the primary loop and rotating the clip to twist the portion, and aligning the clips of different primary loops so that a magnetized portion of a clip having a first polarity is aligned with a magnetized portion of an adjacent clip having a second polarity.

The method includes moving the coil relative to the clip and using the clip to twist each of the one or more primary loops in turn to form a corresponding secondary loop.

The method includes positioning the coil about a helical groove of an elongated member, and moving the coil relative to the clip by rotating the elongated member.

Twisting a portion of the primary loop to form the secondary loop includes gripping a portion of the primary loop using a hook and rotating the hook to twist the portion of the primary loop.

After formation of the secondary loop, the combination of the primary loop and the secondary loop has a dimension that is smaller or equal to a dimension of the primary loop prior to formation of the secondary loop, the dimensions being measured along a lateral direction at an angle to the longitudinal direction, the dimension of the combination of the primary loop and the secondary loop being defined as the diameter of a bounding circle of the primary and secondary loops, and the dimension of the primary loop being defined as the diameter of a bounding circle of the primary loop.

The secondary loop includes a peripheral loop.

The secondary loop includes an endoloop.

The method includes inserting an elongated member into the coil, for each of the one or more primary loops, urging a first portion of a primary loop towards the elongated member to cause a second portion of the primary loop to move away from the elongated member, providing more space to manipulate the second portion of the primary loop to form the secondary loop.

The coil includes at least one of biodegradable polymeric material, non-biodegradable polymeric material, metal alloy, and ceramic material.

The method includes, for all of the primary loops, forming a secondary loop on the primary loop.

After formation of the secondary loop, the medical apparatus has a dimension that is bound by a first bounding cylinder, which is smaller than a second bounding cylinder that bounds the coil prior to formation of the secondary loops.

The method includes forming two or more secondary loops for each of the one or more primary loops.

The secondary loop may include a closed loop or a partially open curve that does not form a closed loop.

The method includes attaching a fiber to a primary loop after formation of a corresponding secondary loop to maintain the shape of the primary and secondary loops, the fiber extending in the longitudinal direction.

Attaching the fiber to the primary loop includes injecting a first gas stream towards the fiber and a portion of the primary loop to heat the fiber and the portion of the primary loop.

The first gas stream is configured to heat the fiber and the wire to a temperature close to but lower than the melting point of the fiber and/or primary loop cause the fiber and/or the portion of the primary loop to soften.

The first gas stream includes an intermittent gas stream.

The method includes urging the fiber against the portion of the primary loop.

Urging the fiber against the portion of the primary loop includes using a second gas stream to urge the fiber against the portion of the primary loop, the temperature of the second gas stream is configured to cause the fiber and the heated portion of the primary loop to solidify.

The method includes using a laser beam to heat the fiber and the portion of the primary loop.

The method includes winding a wire around an elongated member to form the coil.

The elongated member has a longitudinal axis and a cross-section having a circumference with first portions that are bound by a first bounding circle and second portions that are bound by a second bounding circle, the second bounding circle being within the first bounding circle.

Winding the wire around the elongated member causes each of the one or more primary loops to have first portions that are bound by the first bounding circle and second portions that are bound by the second bounding circle.

The method includes forming the secondary loop from one of the first portions of the primary loop.

Providing the coil includes cutting an elongated tube along a helical path.

The helical path has a variable pitch.

A longitudinal axis of the helical path substantially coincides with a longitudinal axis of the elongated tube.

The elongated tube includes at least one of biodegradable polymeric material, non-biodegradable polymeric material, metal alloy, ceramic material, and composite materials.

Cutting the elongated tube includes directing a laser beam along a helical path on the surface of the elongated tube to cut the tube into the coil.

Cutting the elongated tube includes directing a liquid jet along a helical path on the surface of the elongated tube to cut the tube into the coil.

Cutting the elongated tube includes using a roller blade to cut the tube.

Cutting the elongated tube includes using more than one roller blades to cut the tube to simultaneously produce more than one coil.

Cutting the elongated tube includes using a knife having a cutting tip with curved edges.

The method includes treating the coil after cutting so that the surface of the coil becomes smoother.

Treating the coil includes heating and softening the coil to reduce edges on the coil.

The elongated tube has a diameter in a range from 0.5 to 80 mm.

The elongated tube has a cross section having at least one of circular, oval, triangular, square, and rectangular shape.

The elongated tube has a cross-section having a circumference with first portions that are bound by a first bounding circle and second portions that are bound by a second bounding circle, the second bounding circle being within the first bounding circle.

Providing the coil includes extruding a material from a container to form the coil.

The method includes moving the container in a specified motion to form a coil having a circular, oval, triangular, rectangular, or polygonal cross section.

In general, in another aspect, the invention features a method that includes generating a medical apparatus having a small-dimension state and a large-dimension state, the small-dimension state being formed by providing a coil including a plurality of primary loops positioned along a longitudinal direction, for each of one or more of the primary loops, forming one or more secondary loops on the primary loop, and attaching one or more longitudinal fibers to the primary loops to tend to maintain the relative positions of the primary loops in the small-dimension state and the large-dimension state.

In general, in another aspect, the invention features a method that includes generating a medical apparatus having a small-dimension state and a large-dimension state, including extruding a material from a container and moving the container in a specified motion so that extruded material forms a coil including a plurality of primary loops positioned along a longitudinal direction, each of one or more of the primary loops having one or more secondary loops, and attaching one or more longitudinal fibers to the primary loops to tend to maintain the relative positions of the primary loops in the small-dimension state and the large-dimension state.

Implementations of the invention may include the following feature. The material includes shape memory alloy.

In general, in another aspect, the invention features a method that includes providing a coil having primary loops, each of one or more primary loops having one or more peripheral loops; and bending one of the peripheral loops towards a central portion of the coil to form an endoloop.

In general, in another aspect, the invention features an apparatus that includes an expandable medical apparatus including a coil having a plurality of primary loops positioned along a longitudinal direction, each of one or more of the primary loops having one or more secondary loops on the primary loop, the distance between adjacent primary loops being different at different portions of the coil.

Implementations of the invention may include one or more of the following features.

The apparatus includes one or more longitudinal fibers attached to the primary loops to tend to maintain the relative positions of the primary loops.

The coil includes at least one of biodegradable polymeric material, non-biodegradable polymeric material, metal alloy, ceramic material, and composite material.

A first portion of the coil where adjacent primary loops are spaced apart at smaller distances has a larger resistance to deformation due to pressure exerted from outside of the coil, as compared to a second portion of the coil where adjacent primary loops are spaced apart at larger distances.

In general, in another aspect, the invention features an apparatus that includes means for supporting a tube, means for cutting a tube to form a coil having primary loops, and means for forming one or more secondary loops from each of one or more primary loops.

Implementations of the invention may include one or more of the following features.

The supporting means includes a rod that is inserted into the tube.

The supporting means includes an elongated screw that in inserted into the tube, the elongated screw having sharp edges.

The supporting means includes a plurality of knives, each having curved cutting edges. The cutting means includes two or more knives positioned side-by-side to cut the tube simultaneously.

DESCRIPTION OF DRAWINGS

FIGS. 5A-5C show a coil formed by winding a wire around a cylinder.

FIGS. 6A-6B show a coil formed by cutting a tube along a helical path.

FIG. 7 shows a cross section of the coil that is rounded to form a circular shape after being cut from the tube.

FIGS. 8A-8C show tubes and coils having different cross sections.

FIGS. 9A-9G, 10A-10F, 11A-11D and 12A-12J show formation of secondary loops.

FIGS. 14A, 15A, and 16A show apparatus for cutting a tube.

FIGS. 14B, 15B, and 16B-16D show cross sections of coils formed by using different types of knives to cut the tube.

DETAILED DESCRIPTION

Figure 1A:
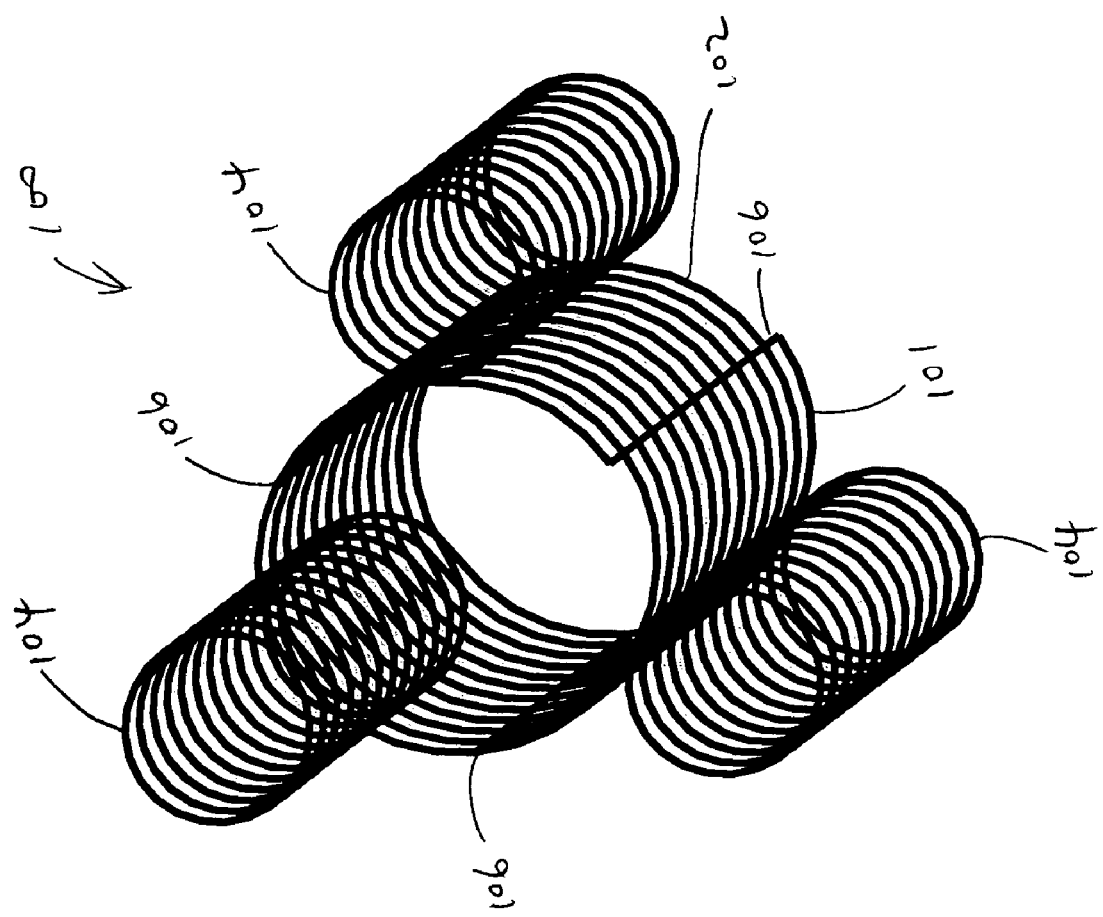
FIGS. 1A and 1B show peripheral expandable stents.

Referring to FIG. 1A, a multi-loop expandable stent 100 includes a coil 101 having twelve primary loops 102, each including three secondary loops 104. The primary loops 102 are positioned along a longitudinal direction of the stent 100. Longitudinal fibers 106 are attached to the primary loops 102 to provide support and to maintain the overall structure of the stent 100 as the stent is inserted into body lumens.

Figure 1B:
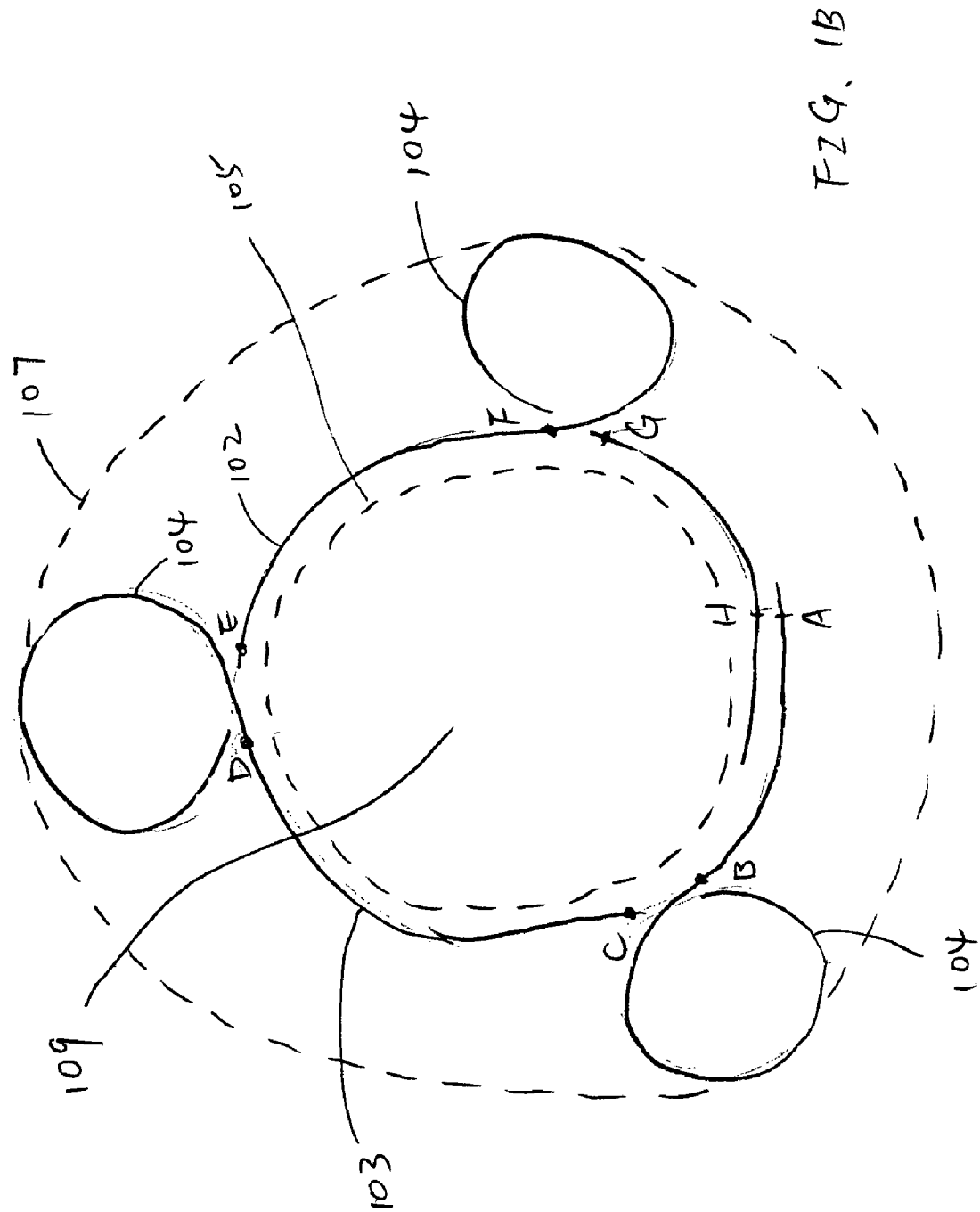

FIG. 1B shows the configuration of a primary loop 102 and its three secondary loops 104. The primary loop 102 includes the structure formed by segments A-B, B-C, C-D, D-E, F-F, F-G, and G-H. The secondary loops 104 include the structure formed by segments B-C, D-E, and F-G. A secondary loop 104 can be an open curve, so that points B and C (or points D and E, or points F and G) do not overlap. Conversely, a secondary loop 104 can be a closed loop, so that points B and C overlap.

The coil 101 has an outer dimension defined as a diameter of an outer bounding circle 107, which is the smallest outer circle that bounds the primary loop 102, including the secondary loops 104. The coil 101 has an inner dimension defined as a diameter of an inner bounding circle 105, which is the largest inner circle that can be bound by segments of the primary loop not forming the secondary loops, such as segments A-B, C-D, E-F, and G-H.

In one example, the coil 101 and the fibers 106 are made of polymers, which can be biodegradable or non-biodegradable. Other materials, such as metal alloy, ceramic or composite materials, can also be used for the coil 101, the fibers 106, or both. Examples of biodegradable polymers include poly(L-lactic acid) and related co-polymers, such as poly(lactic-co-glycolic acid) (PLGA) and poly(epsilon-caprolactone and l-lactic acid). An example of a non-biodegradable polymer is expanded polytetrafluoroethylene (ePTFE). Examples of metal alloys include stainless steel and cobalt-chromium. An example of a ceramic material is titanium-nitride-oxide. An example of a composite material is poly(ethylene oxide)/polyurethane.

Figure 2A:
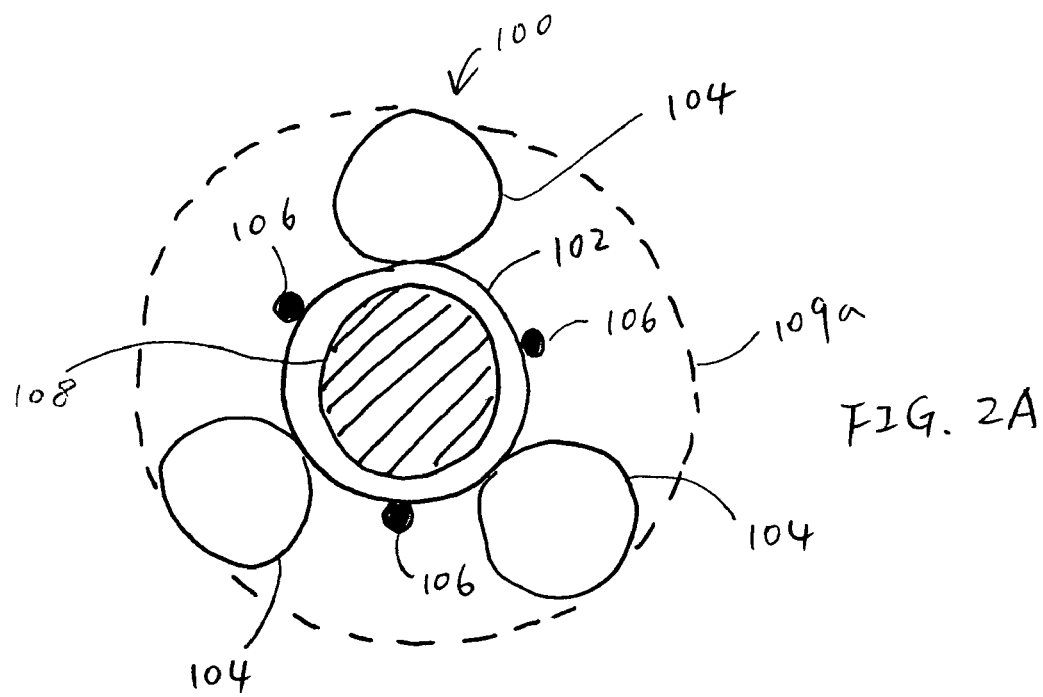
FIGS. 2A-2C show the transition of the stent from a small-dimension state to a large-dimension state.
Figure 2B:
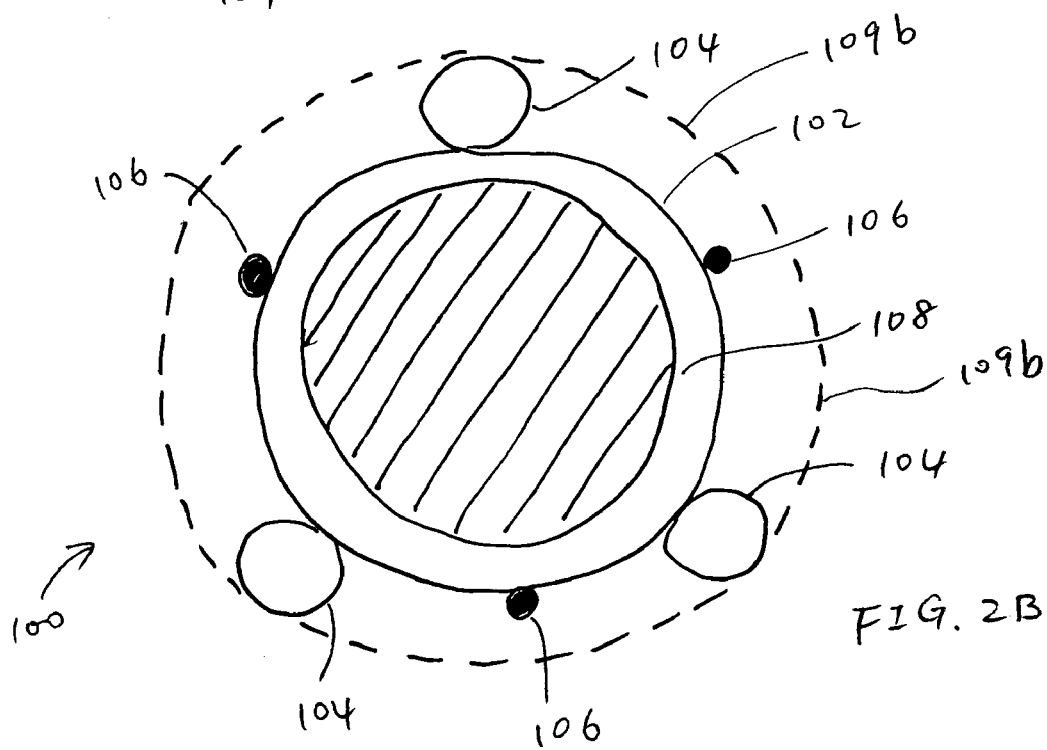
Figure 2C:
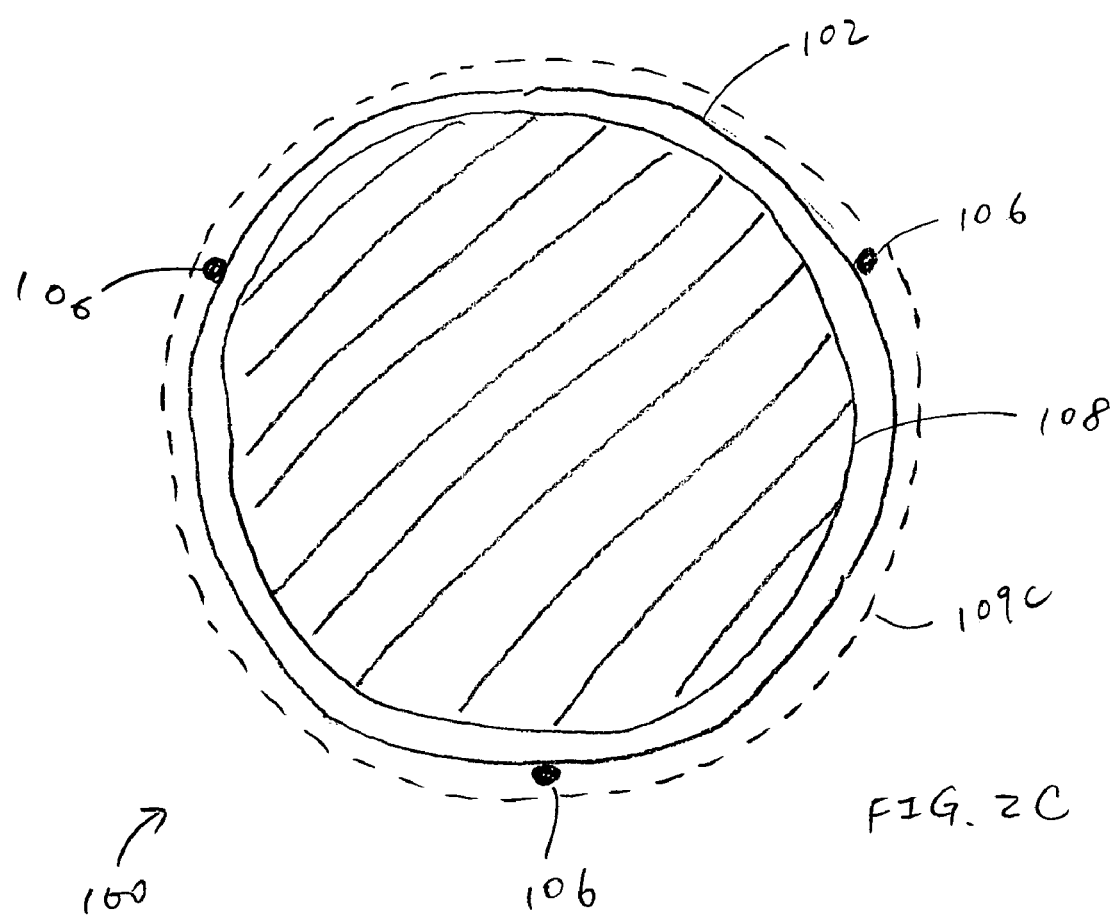

FIGS. 2A-2C show the transition of the stent 100 from a small-dimension (collapsed) state (as shown in FIG. 1A) to a large-dimension (expanded) state. Only one primary loop and three secondary loops are shown. A balloon 108 is inserted into the primary loop 102 (FIG. 2A). As the balloon 108 inflates (FIG. 2B), the dimensions of the secondary loops 104 are reduced while the dimension (inner dimension and outer dimension) of the primary loop 102 is increased. When the balloon 108 is fully expanded (FIG. 2C), the secondary loops 104 disappear, leaving only an expanded primary loop 102.

In one example, prior to balloon expansion, the primary loop 102 has an inner dimension ranging from 0.05 mm to 70 mm, and each secondary loop 104 has a diameter ranging from 0.01 mm to 50 mm. To illustrate the variation in dimension of the stent, a bounding cylinder that bounds the outer edges of the stent is used to represent the size of the stent. As shown in FIG. 2A, the stent 100 is bound by a bounding cylinder 109a (shown in dashed line), which can have a diameter ranging from 0.05 mm to 85 mm, depending on the sizes of the secondary loops and the inner dimensions of the primary loops. This allows the stent 100 to pass through a body lumen having a diameter of large than 0.1 mm. As the balloon 108 inflates, the diameter of the bounding cylinder increases, as represented by 109b and 109c in FIGS. 2B and 2C, respectively. When the stent is fully expanded, the bounding cylinder 109c has a diameter ranging from 0.11 mm to 100 mm, depending on the number of the secondary loops and the size of the stent.

Comparing FIGS. 2A and 2C, the stent (in its small-dimension state) can be inserted into a body passageway having a dimension smaller than the bounding cylinder 109c and larger than the bounding cylinder 109a. By expanding the stent, the passageway can be expanded to have a dimension comparable to the bounding cylinder 109c.

Figure 3:
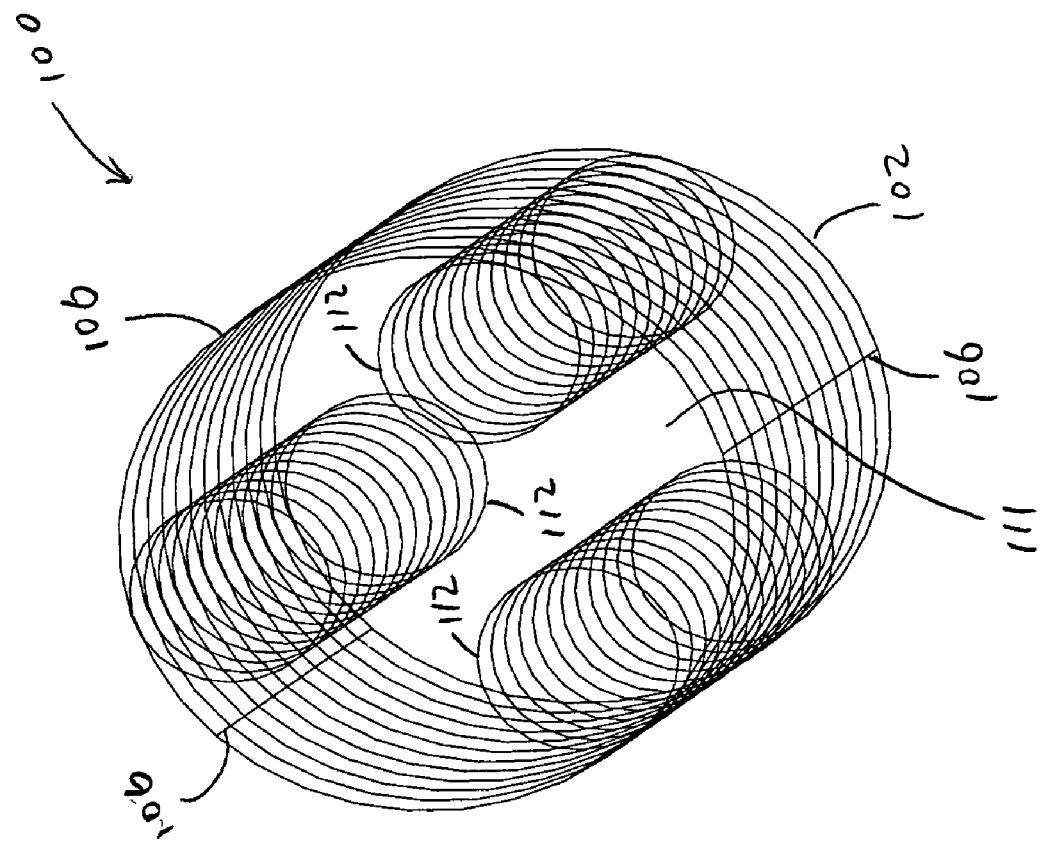
FIG. 3 shows an endoloop stent that includes primary loops and secondary loops.

In the example shown in FIGS. 1A and 1B, the secondary loops 104 are peripheral loops positioned outside of the space 109 formed by other portions (e.g., segments A-B, C-D, E-F, and G-H) of the primary loops 102. Referring to FIG. 3, an example of an endoloop stent 110 includes primary loops 102 and secondary loops 112 that are endoloops positioned within the space 111 formed by other portions of the primary loops 102.

Figure 4:
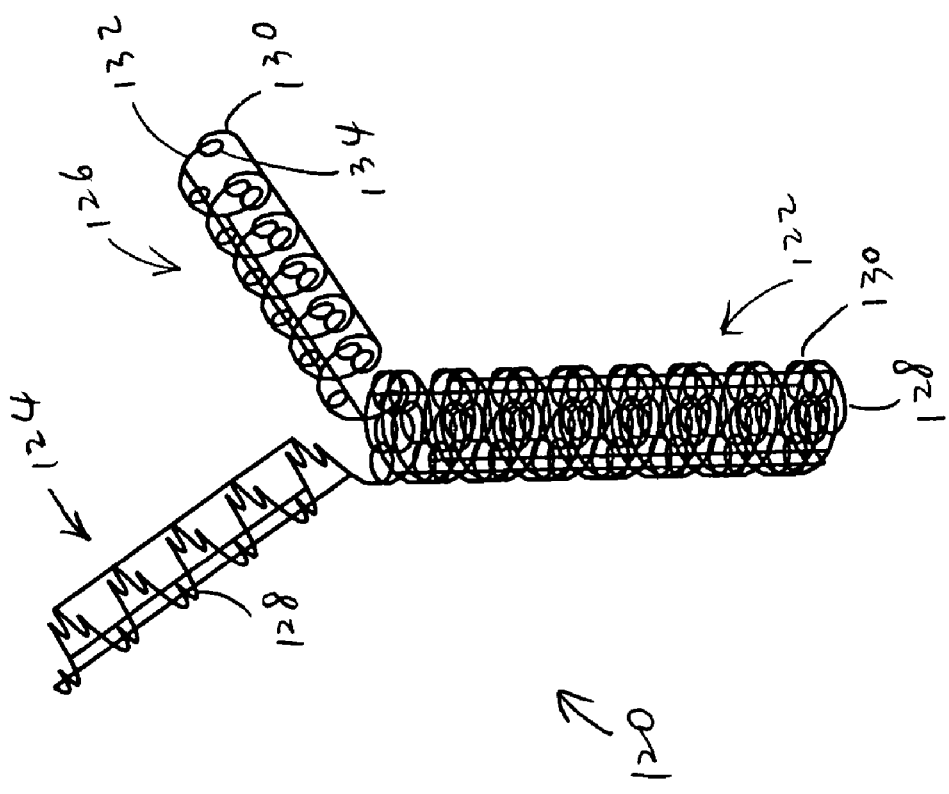
FIG. 4 shows a bifurcated stent.

Referring to FIG. 4, an example of a bifurcated stent 120 includes a first arm 122, a second arm 124, and a third arm 126. The first arm 122 includes a first coil 128 and a second coil 130. The first and second coils overlap in the first arm 122, and bifurcates to form the second arm 124 and the third arm 126. Each of the first and second coils have primary loops (e.g., 132) and secondary loops (e.g., 134). The stent 120 can be used at a junction of two arteries.

The following describes different methods of forming a coil, which can be used to generate a stent having primary loops and secondary loops (e.g., peripheral loops or endoloops).

Referring to FIGS. 5A-5C, a straight wire 140 is wound around a cylinder 144 in a helix (FIG. 5B) to form a coil 142 (FIG. 5C). The wire can be made of polymeric materials (including biodegradable and non-biodegradable polymers), metallic materials, or ceramic materials that have proper diameter with suitable strength. In FIG. 5C, the helix has a pitch "p" that refers to the distance between adjacent primary loops. The pitch can be constant throughout the length of the coil, or be variable.

When a stent has a fixed pitch, the strength of the stent after expansion is constant along its longitudinal axis. Such a stent is useful when applied to a lesion site that has uniform morphology.

By using a stent having variable pitch, the stent can have stronger structures at specific sections of the stent. The portion of the stent with a smaller pitch will be stronger than a portion with a larger pitch. The smaller-pitch portion has a greater resistance to deformation due to force exerted on the coil, either from outside of the coil towards the inside, or from inside of the coil towards the outside along a radial direction. The smaller-pitch section can be placed at a narrower lesions of the artery to provide greater support strength.

Referring to FIGS. 6A-6B, a coil can be made by cutting a tube 146 along a helical path 148 extending from one end 150 of the tube 146 to another end 152 of the tube. The tube can be cut using a thin blade or a laser beam, or a high-pressure liquid jet, or using a combination of the above. When a liquid jet is used, the liquid can be water or a solvent that can dissolve the tube material. An advantage of using the liquid jet is that, the liquid jet cuts the tube without heating the tube material (which may cause the material property to change). The liquid can also be liquid nitrogen, liquid carbon dioxide, or liquid argon, etc. By using liquid state of materials that become gas at room temperature, there will be no residual material after the cutting process is completed. FIG. 6B shows the coil 148 after the tube 144 has been cut.

The helical path 148 can have a fixed pitch or a variable pitch. When a variable pitch is used, the stent can have stronger structures at specific sections of the stent.

In the example of using a thin blade to cut the tube, the blade can be mounted on an L-shaped knife. The longer leg of the L-shaped knife is held against the tube for support, and the shorter leg of the L-shaped knife includes the thin blade that cuts into the tube. In one example, the tube is stationary, and the blade follows a helical path to cut the tube. In another example, the tube is rotated, and the blade moves relative to the tube in the longitudinal direction to cut the tube.

Figures 14A, 14B:
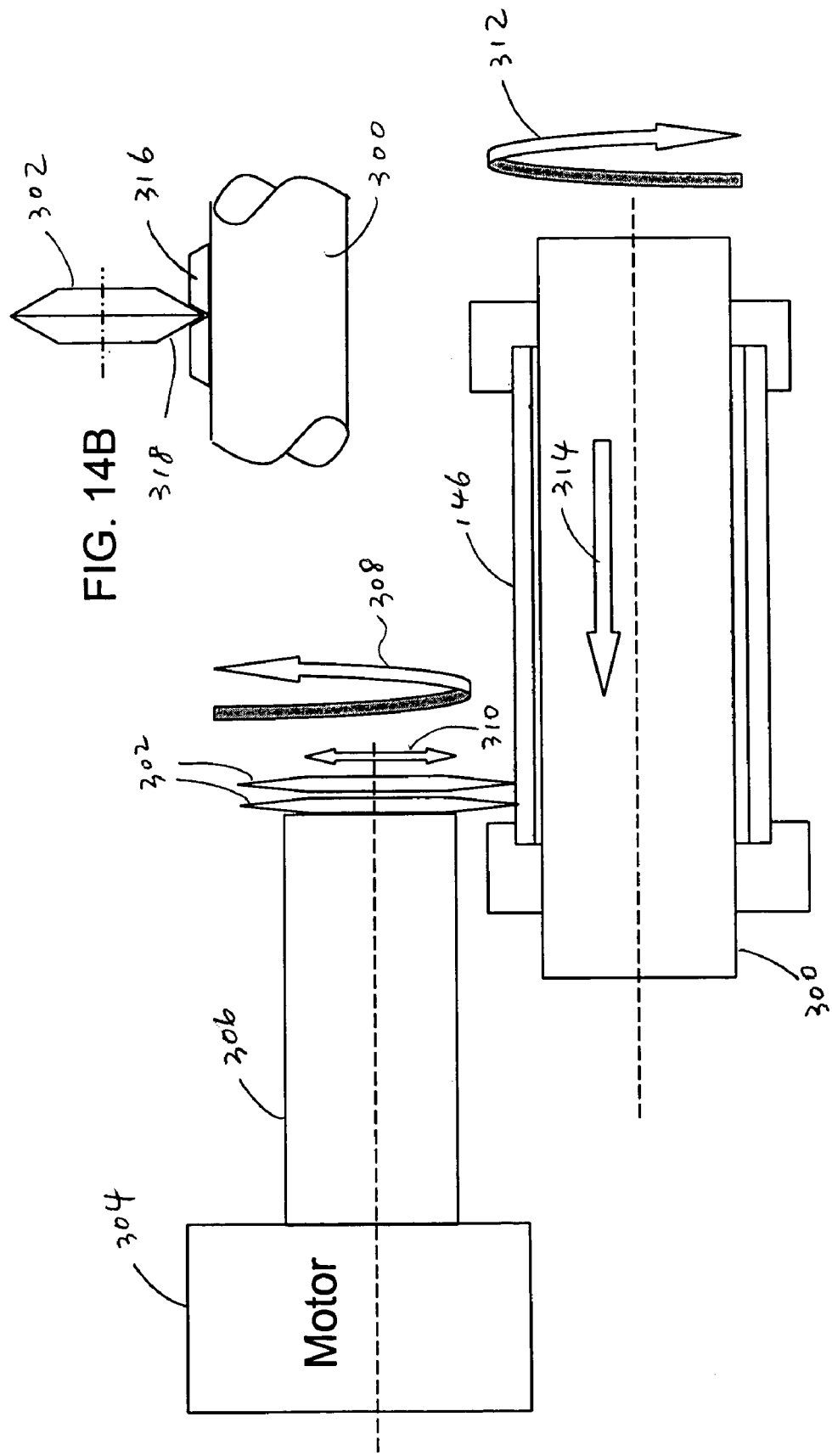

Referring to FIG. 14A, another way to cut the tube 146 is to insert a rod 300 into the tube 146, and use one or more sharp knives 302, such as roller knives, to cut through the tube material. The cross section of the rod 300 depends on the cross section of the tube 146. For example, if the tube 146 has a triangular cross section, the rod 300 would have a triangular cross section. Similarly, if the tube 146 has a circular cross section, the rod 300 would have a circular cross section. The rod 300 prevents the knife 302 from cutting through the other side of the tube and provides support during the cutting process. The sharp knives 302 are attached to a motor 304 through a shaft 306. The knives 302 are initially positioned above the tube, then pushed down along a direction represented by arrow 310 so that the knives 302 press into the tube material. The motor rotates the knives 302 in a direction represented by the arrow 308.

The rod 300 also rotates along a direction represented by an arrow 312, which is opposite to the direction represented by arrow 308 (one being clockwise, the other being counter-clockwise). The rod 300 also moves along a direction represented by arrow 314, which is parallel to the longitudinal axis of the tube 146. The combination of the movement in the direction 314 and rotation in the direction 312 causes the knives 302 to cut the tube material along one or more helical paths. The speed at which the rod 300 move along direction 314 determines the pitch of the coil.

If one sharp knife 302 is used, one coil will be produced. If two sharp knives 302 are used, two coils will be produced at the same time. If three sharp knives 302 are used, three coils will be produced at the same time, and so forth.

FIG. 14B shows a knife 302 cutting into the tube material. When the knife 302 has straight edges, the cross section 316 of the coil will have a near-rectangular or trapezoidal shape.

Referring to FIG. 15A, in another example, a screw 320 with sharp tips 322 is inserted into the tube 146. The size of the tube is selected to be large enough to accommodate the screw 320. The screw 320 can be replaced by roller blades mounted on a shaft.

Referring to FIG. 15B, as the knife 302 presses into the tube 146, the tube is cut from both sides. When the knife 302 and the screw tip 322 have straight edges, the cross section 324 of the coil will have a hexagonal shape.

Figure 16A:
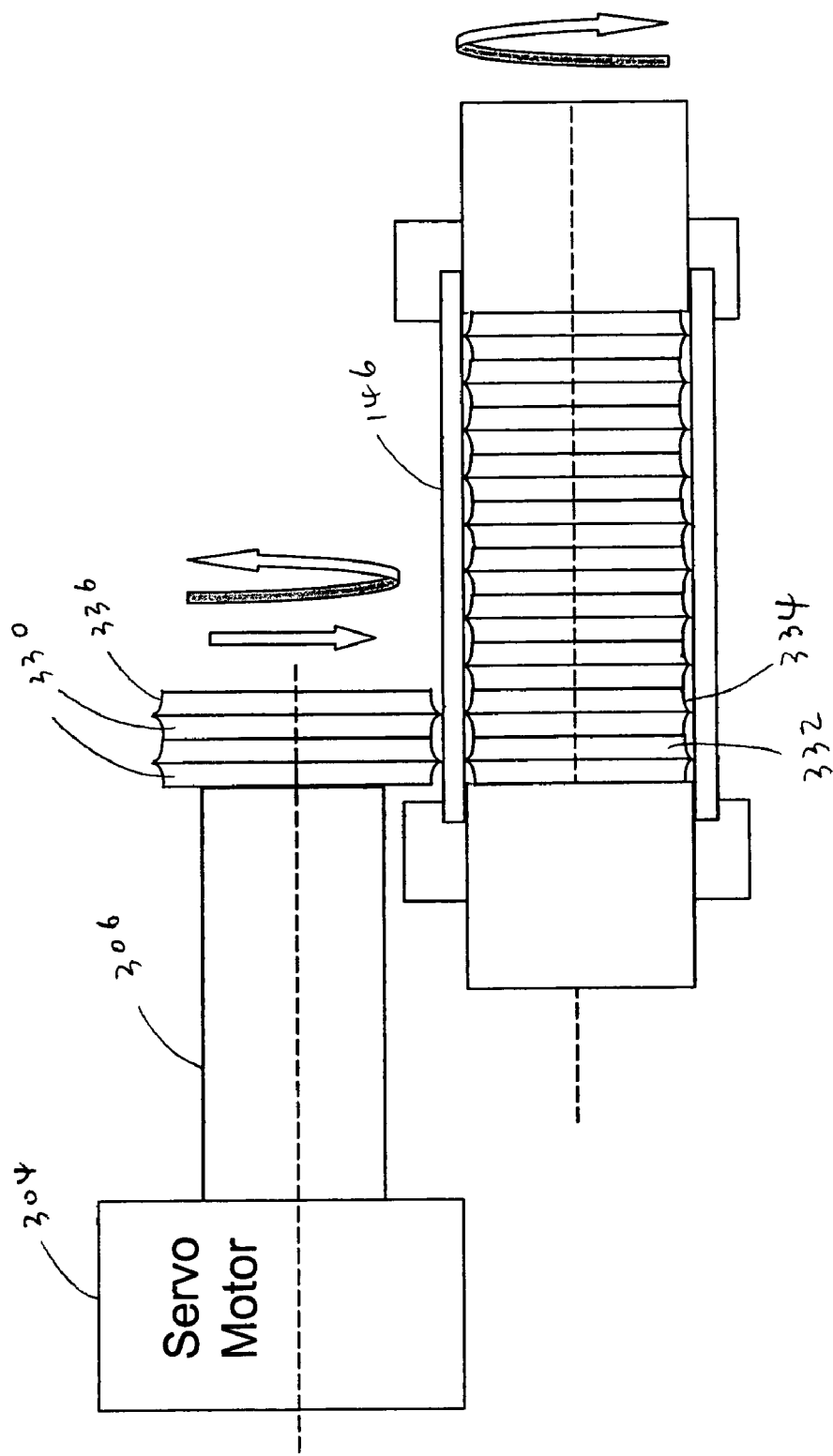
Figure 16D:
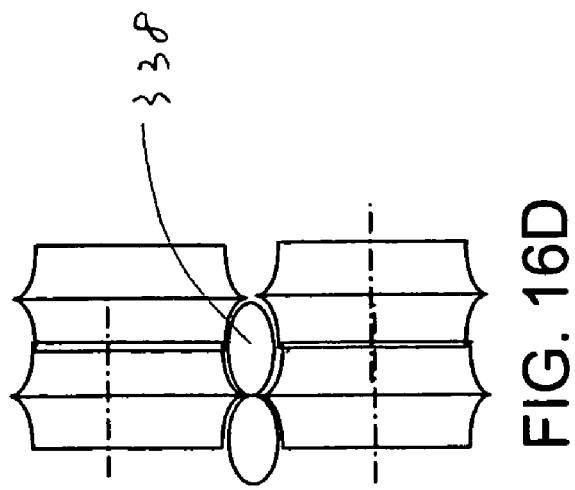
Figure 16C:
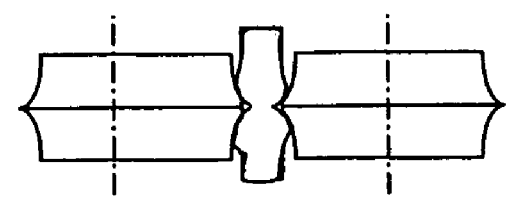
Figure 16B:
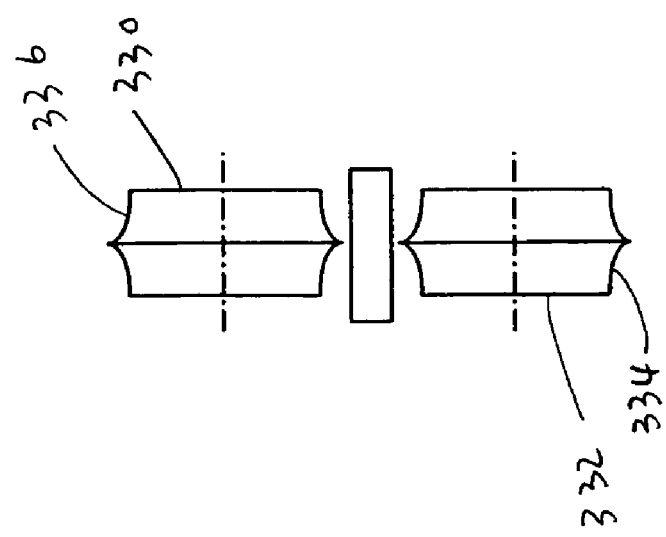

Referring to FIG. 16A, in another example, circular blades 332 having curved cutting edges are inserted into the tube 146. Circular blades 330 having curved cutting edges 336 are connected to the motor 304 through the shaft 306. As shown in FIGS. 16B to 16D, when the outer blades 330 and the inner blades 332 cut into the tube, the resulting coil will have a cross section 338 having an oval or circular shape.

Using blades with curved edges is useful when producing coils that have a larger cross section. For example, the outer diameter of a stent for use in the colon can be about 80 mm, and the thickness of the tube for producing the coil can be more than 1 mm. The coil, after being cut from the tube, will already have an oval or circular shape, making it easier to smooth the surface of the coil by using a solvent or by heating the coil.

Referring to FIG. 7, the cross section 160 of the coil 148 (FIG. 6B) may have a rectangular shape, hexagonal, or oval shape, depending on the shape of the tip of the cutting knife. After being cut from the tube 146, the surface of the wire may have corners (e.g., 164). Applying heat to partially melt the coil 148 can make the cross section smoother, or rounder without corners, as shown in the cross section 162. This allows the stent 100 to pass through body lumens more easily. A stent having a smoother surface, when inserted into a blood vessel, will cause less turbulence in the blood stream.

The surface of the coil can also be made smoother by using solvent treatment. The coil is immersed into a solvent, either in liquid or vapor form, which causes the outer surface of the stent to be dissolved. Due to the surface tension of the solvent, a rounder edge will be form. After a preset time, heat is applied to evaporate the solvent.

In FIGS. 6A-6B, the tube 146 has a circular cross section, and the coil 148 cut from the tube has circular-shaped primary loops. Tubes having other shapes of cross sections can also be used. For example, as shown in FIG. 8A, a tube 170 having an oval cross section 172 can be cut into a coil 174 with oval primary loops. In another example, as shown in FIG. 8B, a tube 180 having a triangular cross section 182 can be cut into a coil 184 with triangular primary loops.

In another example, as shown in FIG. 8C, a tube 190 with a user-defined cross section 192 can be cut into a coil 194 having primary loops with the user-defined shape. A feature of the shape 192 is that portions 195 are closer to the center 196 of the cross section, and portions 197 are farther from the center 196. The center 196 is defined as the center of an inner bounding circle 198 of the cross section 192. This configuration allows a user to more easily manipulate the coil because when an elongated member is inserted into the coil for support, there will be more space between the elongated member and the portions 197, so that it is easier to twisting the portions 197 to form the secondary loops.

The polymeric materials used to make the wire 140 or tubes 146, 170, 180, and 190 can incorporate drugs, such as anti-oxidant, antiplatelet, anti-inflammation, anti-smooth muscle proliferation, cytokine antagonizer, vessel dilator, extracellular matrix metalloproteinase inhibitor, and immune depressant type pharmaceutical agents, with polymer in extrusion or injection. For example, in the process of making wire 140, or tube 146, 170, 180 and 190, the drugs mentioned above are first compounded with polymer resins. Compounded polymer-drug materials are then used for the melting extrusion and injection. The extruded or injected products are then drawn to reach mechanical strength requirement. The surface of the stents, including polymeric, metallic, or ceramic stents, can also be modified or coated with drug reservoirs to carry, for example, DNAs, RNA interference (siRNAs, miRNAs, stRNAs, or shRNAs) peptides, and proteins for specific therapeutic functions.

Figure 9:
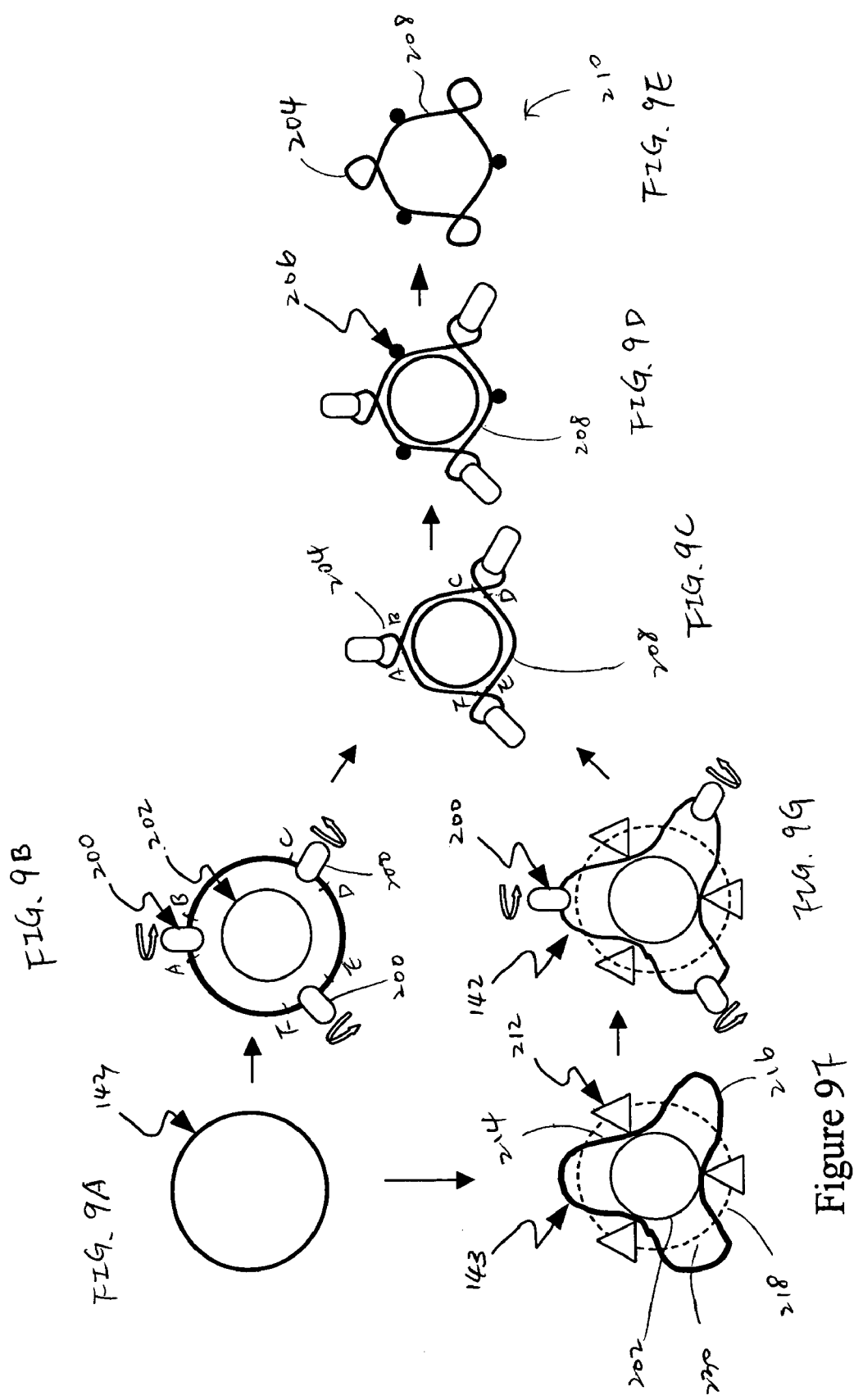

Referring to FIGS. 9A-9D, the coils 142, 148, 174, 184, and 194 can be manipulated to produce multiple secondary loops. In the description below, only one primary loop is shown (FIG. 9A). In the first method, three clips 200 (or grippers, hooks) are used to grip portions A-B, C-D, and E-F of a primary loop 143 (FIG. 9B). The spacing between the clips 200 can be even or uneven, and the number of the clips is not limited to three. A rod 202, either with an expandable or fixed circumference, is inserted into the primary loop 143 for support. The cross section of the rod 202 can have a shape of, for example, a circle, a triangle, a square, a rectangle, an oval, or a polygon.

Referring to FIGS. 9B-9C, the three clips 200 (or grippers, hooks) are simultaneously or sequentially rotated to twist the segments A-B, C-D, and E-F of the primary loop 143 to form three secondary loops 204. The clips can rotate, for example, 90 degrees, to from open curve secondary loops. The clips can rotate, for example, 180 degrees, to form closed secondary loops. The number of secondary loops 204 is determined by the number of clips 200.

Referring to FIG. 9D, three longitudinal fibers 206 are attached to the exterior of the primary loop 208. Referring to FIG. 9E, After the longitudinal fibers 206 are secured, clips 200 are released, resulting in a stent 210 having three secondary loops 204 corresponding to each primary loop 208. The secondary loops 204 will be folded down about 90 degrees along the direction of the longitudinal axis of the stent and put into a thin sleeve or cylinder to hold the shape.

To produce a stent with endoloops, the primary loops are stretched in sequence along its longitudinal axis, and the secondary loops are folded more than 90 degree one by one. After the secondary loops are folded, the stretched primary loops are placed back to its original shape, with the secondary loops inside the primary loops. In this example, the rod 202 is designed so that its circumference is adjustable. Initially, when the secondary loops are formed according to the process shown in FIGS. 9B-9D, the rod is in an expanded state. Prior to folding the secondary loops into endoloops, the rod 202 is changed to a collapsed state with a smaller circumference. The rod 202 is removed after the stent 210 is placed into a storage package, sleeve or cylinder, (not shown).

A second method of forming the secondary loops 204 is shown in FIGS. 9F and 9G. Referring to FIG. 9F, a set of blocks 212 are used to urge portions (e.g., 214) of the primary loop 143 toward the rod 202. When portions 214 of the primary loop 143 is urged towards the rod 202, portions 216 of the primary loop will extend outwards (as compared to the dashed line 218 showing the original position of the primary loop. This results in a larger space 230 between portions 216 and the rod 202, making it easier for the clips 200 to manipulate the portions 216 to form the secondary loops.

Referring to FIG. 9G, the clips 200 are rotated to form the secondary loops 204. Longitudinal fibers are attached to the outer side of the primary loop 208, and the clips are released, resulting in a stent having primary loops and secondary loops (similar to the process shown in FIGS. 9C to 9E). The method shown in FIGS. 9F and 9G can be used when the diameter of the primary loop 143 is small.

An advantage of using the method of FIGS. 9F and 9G is that the stent has a circular cross section when expended, while at the same time, the coil is easy to manipulate to form the secondary loops. Circular shaped stents tend to have stronger structures, as compared to non-circular shaped stents, such as the one shown in FIG. 8C. Circular stents are suitable for most body passageways, such as the artery, which have circular cross sections. If a particular body passageway has a non-circular cross section, a coil can be made from a tube having a cross section with the non-circular shape. A stent formed by the coil will conform to the contours of the passageway after expansion.

FIGS. 10A-10F show a process of using a coil 194 with primary loops having a user-defined shape that allows easier manipulation of the primary loop by using clips. Coil 194 has portions 197 farther away from a longitudinal axis 201. FIGS. 10A, 10C, and 10E show front views of the coil 194 in which the longitudinal axis 201 is perpendicular to the plane of the figures. FIGS. 10B, 10D, and 10F show side views of the coil 194 in which the longitudinal axis 201 is parallel to the plane of the figures.

As shown in FIGS. 10A and 10B, an array of clips 240 (three clips for each primary loop), are used to manipulate the coil 194 to form the secondary loops. Referring to FIGS. 10C and 10D, an expandable center rod 202 is inserted into the coil 194 to provide support. The function of expandable center rod 202 is facilitate easy loading and unloading of the coil, for example, 143 or 194. Each clip 240 rotates and twists portions of the coil 194 to form the secondary loops 242. The clips can rotate, for example, in a range of 90 to 270 degrees, to form the secondary loops.

Referring to FIGS. 10E and 10F, three longitudinal polymeric fibers 206 are attached to the exterior of the primary loops to maintain the positions of the primary loops relative to one another. In one example, the longitudinal fiber is stretched, using clips to hold the two ends of the fiber. The fiber is then pushed directly against the coil. The longitudinal fiber can be attached on one side (such as the outside or inside) of the coil. The longitudinal fiber can also be woven into the stent structure. For example, the fiber can attach to the outer side of the first primary loop, to the inner side of the second primary loop, to the outer side of the third primary loop, and so forth.

FIGS. 11A-11D show another process for fabricating a stent using the coil 194, which has extended portions 250 farther away from a central longitudinal axis. FIGS. 11A and 11C show front views of the coil 194 in which the longitudinal axis of the stent is perpendicular to the plane of the figures. FIG. 11C is seen along a cross section represented by lines 11A-11A, and shows the coil after the secondary loops are formed. FIGS. 11B and 11D show side views of the coil 194 in which the longitudinal axis of the stent is parallel to the plane of the figures.

Three clips 260 are used to manipulate one primary loop at a time to form secondary loops. The clips 260 are positioned in proximity to the extended portions 250. These clips operate in cooperation with a rotating rod 252 having a helical ridge 254. As the rod 252 rotates clockwise (as viewed from the right end 253 of the rod 252 towards the left end 255 of the rod), as shown by an arrow 256, the helical ridges 254 push the coil 194 towards the left, as shown by arrow 258. The speed of movement of the coil 194 depends on the speed of rotation of the rod 252 and the pitch of the spiral ridges 254, and is synchronized with the speed of the clips 200 twisting portions of the coil 194 to form the secondary loops 242.

Rod 252 has a portion 262 with a smaller diameter to provide space for the clips 260 to manipulate the coil 194. The clips 260 grab portions of the coil and rotate certain degrees (e.g., 90 to 270 degrees) to produce the secondary loops 242. As the coil 194 moves left and away from the rod 252, longitudinal fibers 206 are attached to the exterior side of the coil 194 to provide support and to maintain the relative positions of the primary loops.

Referring to FIG. 11D, another method of moving the coil 194 relative to the clips 260 is to use a rod 270 having small blocks 272 that push the coil 194 towards the left, as shown by an arrow 274. The blocks 272 are moved by a conveyor belt. The speed of the moving blocks 272 is synchronized with speed of the clips 260 in forming the secondary loops 242. As the coil 194 moves away from the rod 270, longitudinal fibers 206 are attached to the exterior side of the coil 194.

FIGS. 12A-12D show a process in which a stent having primary loops and secondary loops is produced from a straight wire 140 by first forming the secondary loops along the length of the wire, and then winding the wire (having the secondary loops) around a rod to form a coil.

Referring to FIG. 12A, the wire 140 can be made of polymer, metal, ceramic, or composite material having a proper diameter and sufficient strength. Referring to FIG. 12B, clips 280 are positioned along the length of the wire 140. The distance between each clip 280 can be constant or variable to produce stents having primary loops with constant pitch or variable pitch.

FIGS. 12B-12D show different views of the wire 140 and the clips 280. FIG. 12D represents a view as seen by facing the longitudinal direction of the wire 140. FIGS. 12B and 12C represent views as seen from points P1 and P2, respectively, as shown in FIG. 12D.

In one example, the clips 280 are magnetized to assist in aligning the wire 140 as the wire is wound around a rod to form a coil. In one example, the tips 282 of the clips 280 that contact the wire 140 are magnetized with different polarities. In one example, the magnetic fields of the clips 280 are generated by passing electric current through miniature coils inside the clips. The magnetic fields can be turned on or off by switching the electric current on or off.

Referring to FIG. 12C, the clips 280 holding the wire 140 are rotated certain degrees (e.g., in the range of 90 to 270 degrees). The direction and amount of rotation can be different for each clip 280. FIG. 12c shows an example in which the clips rotate in the same direction. As the clips rotate, secondary loops 284 are formed, as shown in FIG. 12E.

Referring to FIGS. 12F and 12G, the wire 140 and the clips 280 are wound (along the direction shown by arrow 141) around a rod 286 to form a helical coil 288. Referring to FIGS. 12H and 12I (which show the helical coil 288 from different views), in the example in which the clips are magnetized, the magnetized portions of the clips line up so that the pitch of the helix is relatively constant. In the example in which the clips are held by another apparatus, such as guide racks, the apparatus can line up the clips without use of magnetic fields.

Referring to FIG. 12J, longitudinal biodegradable fibers 206 are attached to the exterior side of the coil 288 to provide support. There are several methods of securing the polymeric fibers 206 to the coil 288. One method is to use solvent based glue to glue fiber 206 to the coil 288. Another method is to use a laser micro-welder to weld the fibers to the coil 288. The power of the laser beam is adjusted so that the intensity of the beam does not alter the properties of the polymeric material forming the coil. Laser pulses can be used to lower the overall beam energy level (as compared to a continuous laser beam).

Another method of securing the fibers 206 to the coil 288 is to use a micro air nozzle 290 in combination with an optional laser beam (or infrared beam) to weld the fiber 206 to the coil 288. The micro air nozzle 290 ejects air whose temperature is adjustable. The diameter of the gas outlet of the nozzle 290 depends on the dimension of the fiber 206 and the wire 140, and can be from 5 to 500 μm.

To weld the fiber 206 to the coil 288, the optional air nozzle 290 initially emits hot gas having a temperature close to but lower than the melting point of the fiber 206 and/or the coil 288. The hot gas is directed towards a welding region 294 where the fiber 206 contacts the coil 288. The hot gas is ejected continuously, or as pulses, onto the welding region 294. A laser beam (or an infrared beam) is directed to the welding region 294. The laser beam can heat up regions of the fiber 206 and the coil 288 more precisely.

After the fiber 206 and the coil 288 are heated by the hot gas and the laser beam, a second nozzle 292 injects gas towards the fiber 206 to urge the fiber against the coil 288. By urging the fiber 206 towards the coil 288, the fiber 206 bonds well to the coil 288 without the need to apply glue. The second nozzle 292 emits cold air that cools the welding region 294.

The hot gas from the first nozzle 290 and the laser beam heats the wire 140 and the fiber 206 to their melting point in a way such that only the surfaces of the wires are melted. The laser beam heats the surface of the fiber and wire directly, while the hot gas circulates the heat around the welding region 294 to distribute the heat more evenly, to regions that cannot be directly illuminated by the laser beam.

A feature of using a combination of a laser beam and hot air to weld the fiber 206 to the coil 288 is that this process produces very little by-product. By comparison, if glue were used, there may be leftover glue that forms unwanted strings when the glue nozzle is removed.

A second feature is that the property of the polymeric material at the welding region does not change. By applying temperature-controlled hot gas to the welding region, the surfaces of the coil 288 and the fiber 206 heats evenly, thereby eliminating over-heated hot spots that may damage the biodegradable material if only a laser beam were applied.

A third feature is that, because the surfaces of the fiber 206 and the coil 288 are heated evenly and pressed together, the contact area between the fiber and the coil is larger than if only a laser beam were used.

A fourth feature is that it takes less time for the fiber 206 and the coil 288 to weld together. By applying the cold gas to the welding region 294 after the hot gas is applied to the welding region, the cold gas solidifies the welding spots in a shorter amount of time than if the cold gas were not used.

Figure 13A:
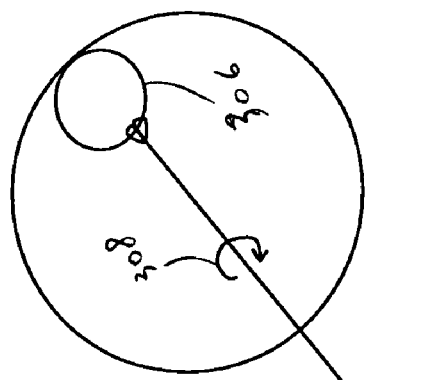
FIGS. 13A-13C show formation of endoloops.
Figure 13B:
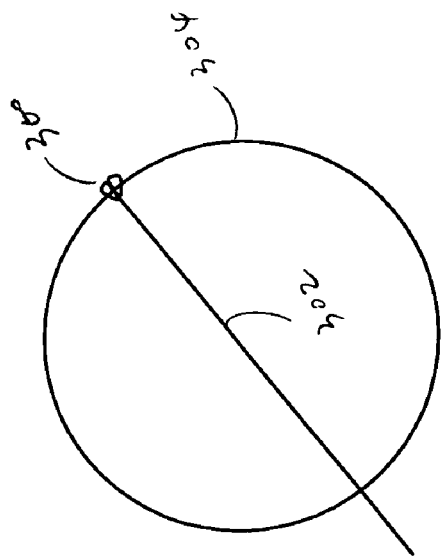
Figure 13C:
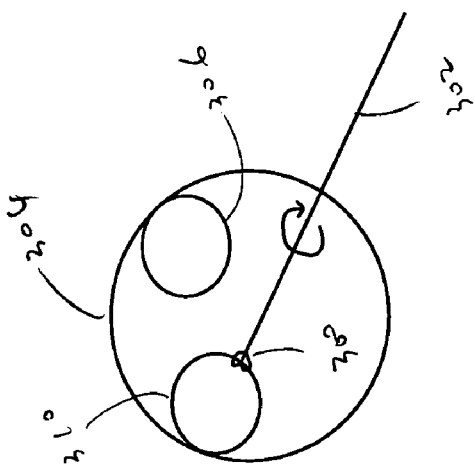

Referring to FIGS. 13A-13C, endoloops can be formed by using a clip 300 (held by an extended handle 302) to grasp a portion of a primary loop 304. As the handle 302 rotates, as shown by the arrow 308, the clip 300 twists the portion of the primary loop to form an endoloop 306. The clip 300 releases the endoloop 306, and grasps another portion of the primary loop. As the handle 302 rotates, the clip 300 twists the other portion of the primary loop to form a second endoloop 310. The process can be repeated to form other endoloops.

Although some examples have been discussed above, other implementations and applications are also within the scope of the following claims. For example, the coil structures shown in FIGS. 1A and 3 are not limited to being used as stents. They can also be used for other therapeutic purposes, such as being used as a scaffold for tissue regeneration. The number of primary loops may vary. Each primary loop can have less than three or more than three secondary loops. Each primary loop can have a mixture of peripheral loops and endoloops. A stent can have some primary loops with peripheral loops and some primary loops with endoloops.

In FIGS. 12B-12J, instead of magnetizing the tips of the clips 280, the handles of the clips 280 (used to maneuver the clips) can be magnetized. The clips 280 can also be manipulated by a machine. For example, clips 280 or the handle of the clips 280 can be designed to attach to racks with actuators or servo motors to perform the motions depicted in FIGS. 12B to 12J.

Figure 17:
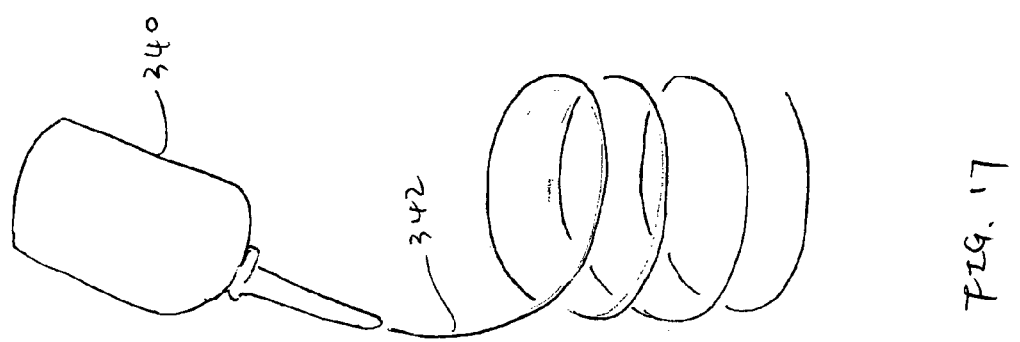

Referring to FIG. 17, rather than producing a coil from a tube (as shown in FIGS. 8A to 8C), a coil can be formed by extruding a material 342 (such as a biodegradable polymeric material, metal alloy, or composite material) from a container 340, and moving the container 340 in a circular (or oval, triangular, rectangular, polygonal, user-defined) motion to produce a coil with circular (or oval, triangular, rectangular, polygonal, user-defined shaped) primary loops.

Figure 18:
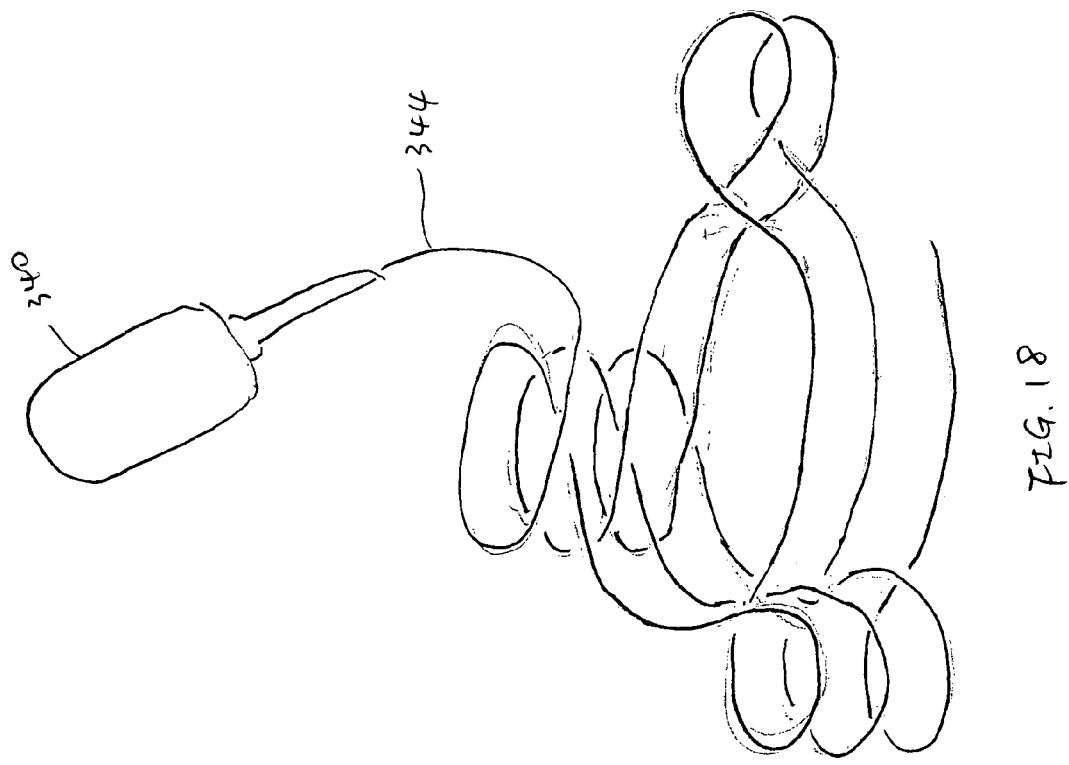
FIGS. 17 and 18 show material being extruded from a container to form coils.

Referring to FIG. 18, the container 340 can also move in a motion so that an extruded material 344 forms primary loops having secondary loops. The material 344 can be, for example, shape memory alloy.

The coil 101 and the fiber 106 can be made of the same material, or of different materials.

What is claimed is:

1. A method comprising:
    generating a medical apparatus by providing a coil comprising a plurality of primary loops along a longitudinal direction, and
    for each of one or more of the primary loops, forming a secondary loop thereon by gripping a portion of the primary loop using a clip and rotating the clip to twist the portion, wherein the clip comprises magnetized portions having different polarities.

2. The method of claim 1, wherein the magnetized portions are disposed at the tips of the clip that contact the primary loop or the secondary loop.

3. The method of claim 1, wherein the clip comprises tips that contact the primary loop and handles that allow manipulation of the clip, the magnetized portions being disposed at the handles.

4. The method of claim 1, further comprising, for each of one or more primary loops, using a clip to grip a portion of the primary loop and rotating the clip to twist the portion, and aligning the clips of different primary loops so that a magnetized portion of a clip having a first polarity is aligned with a magnetized portion of an adjacent clip having a second polarity.

5. The method of claim 1, further comprising positioning the coil about a helical groove of an elongated member, and moving the coil relative to the clip by rotating the elongated member.

6. The method of claim 1, further comprising inserting an elongated member into the coil, for each of the one or more of the primary loops, urging a first portion of a primary loop towards the elongated member to cause a second portion of the primary loop to move away from the elongated member, providing more space to manipulate the second portion of the primary loop to form the secondary loop.

* * * * *